(12) United States Patent
King et al.

(10) Patent No.: US 12,128,078 B2
(45) Date of Patent: Oct. 29, 2024

(54) LYSATES OF RECOMBINANT YEAST FOR INDUCING CELLULAR IMMUNE RESPONSES

(71) Applicant: GLOBEIMMUNE, INC., Louisville, CO (US)

(72) Inventors: Thomas H. King, Denver, CO (US); Zhimin Guo, Superior, CO (US); Courtney Fleenor, Arvada, CO (US)

(73) Assignee: GlobeImmune, Inc., Louisville, CO (US)

(*) Notice: Subject to any disclaimer, the term of this patent is extended or adjusted under 35 U.S.C. 154(b) by 964 days.

(21) Appl. No.: 17/047,134

(22) PCT Filed: May 13, 2019

(86) PCT No.: PCT/US2019/031962
§ 371 (c)(1),
(2) Date: Oct. 13, 2020

(87) PCT Pub. No.: WO2019/222073
PCT Pub. Date: Nov. 21, 2019

(65) Prior Publication Data
US 2021/0154250 A1    May 27, 2021

Related U.S. Application Data

(60) Provisional application No. 62/671,587, filed on May 15, 2018.

(51) Int. Cl.
| | | |
|---|---|---|
| A61K 36/06 | (2006.01) | |
| A61K 39/00 | (2006.01) | |
| C12N 1/06 | (2006.01) | |

(52) U.S. Cl.
CPC .......... *A61K 36/06* (2013.01); *A61K 39/0011* (2013.01); *C12N 1/063* (2013.01); *A61K 2039/572* (2013.01); *A61K 2039/575* (2013.01)

(58) Field of Classification Search
CPC ............... A61K 36/06; A61K 39/0011; A61K 2039/572; A61K 2039/575; A61K 36/00; A61K 39/39; C12N 1/063; C07K 16/2878
See application file for complete search history.

(56) References Cited

U.S. PATENT DOCUMENTS

| | | |
|---|---|---|
| 4,514,506 A | 4/1985 | Braatz et al. |
| 4,775,622 A | 10/1988 | Hitzeman et al. |
| 5,234,830 A | 8/1993 | Oshima et al. |
| 5,310,654 A | 5/1994 | Isberg et al. |
| 5,413,914 A | 5/1995 | Franzusoff |
| 5,550,214 A | 8/1996 | Eberlein et al. |
| 5,648,226 A | 7/1997 | Van den Eynde et al. |
| 5,750,395 A | 5/1998 | Fikes et al. |
| 5,830,463 A | 11/1998 | Duke et al. |
| 5,840,839 A | 11/1998 | Wang et al. |
| 5,858,378 A | 1/1999 | Bostwick |
| 5,919,651 A | 7/1999 | Hitzeman et al. |
| 7,083,787 B2 | 8/2006 | Duke et al. |
| 7,439,042 B2 | 10/2008 | Duke et al. |
| 7,465,454 B2 | 12/2008 | Franzusoff et al. |
| 7,563,447 B2 | 7/2009 | Franzusoff et al. |
| 7,595,060 B2 | 9/2009 | Duke et al. |
| 7,625,569 B2 | 12/2009 | Duke et al. |
| 7,632,511 B2* | 12/2009 | Duke ................ A61P 31/14 435/69.3 |
| 7,736,642 B2 | 6/2010 | Duke et al. |
| 8,821,892 B2* | 9/2014 | Duke ................ A61P 43/00 435/69.3 |
| 8,961,988 B2* | 2/2015 | Apelian ............ A61K 45/06 435/254.2 |
| 9,290,547 B2* | 3/2016 | Apelian ............ A61P 37/04 |
| 9,623,097 B2* | 4/2017 | Palena .............. A61P 13/08 |
| 9,782,473 B2* | 10/2017 | King ................ A61P 31/18 |

(Continued)

FOREIGN PATENT DOCUMENTS

| | | |
|---|---|---|
| EP | 0414404 | 2/1991 |
| FR | 2486400 | 1/1982 |

(Continued)

OTHER PUBLICATIONS

Jacob, D et. al. "Yeast lysates carrying the nucleoprotein from measles virus vaccine as a novel subunit vaccine platform to deliver Plasmodium circumsporozoite antigen", 2017, Malaria Journal, 16(259), 1-14. (Year: 2017).*
Jacob et al. "Yeast lysates carrying the nucleoprotein from measles virus vaccine as a novel subunit vaccine platform to deliver Plasmodium circumsporozoite antigen", 2017, Malaria Journal, 16(259), 1-14. (Year: 2017).*
Banchereau et al., "Dendritic cells and the control of immunity," Nature, 1998, vol. 392, pp. 245-252.
Bernstein et al., "Recombinant *Saccharomyces cerevisiae* (yeast-CEA) as a potent activator of murine dendritic cells," Vaccine, 2008, vol. 26, pp. 509-521.
Bizzini et al. "Use of live *Saccharomyces cerevisiae* cells as a biological response modifier in experimental infections," FEMS Microbiology Immunology, 1990, vol. 64, pp. 155-167.

(Continued)

*Primary Examiner* — Nelson B Moseley, II
*Assistant Examiner* — Alyssa Rae Stonebraker
(74) *Attorney, Agent, or Firm* — Sheridan Ross P.C.

(57) ABSTRACT

Disclosed are immunogenic pharmaceutical compositions comprising yeast lysates for inducing cellular immune responses, methods of making immunogenic compositions comprising yeast lysates, methods of treatment comprising administration of said compositions, and kits comprising said yeast lysate compositions. Disclosed immunogenic compositions further comprise an antigen heterologous to the yeast, and may comprise whole yeast and immunostimulatory agents. Induced cellular immune responses comprise cytotoxic T cell activation with specificity to the antigen comprising the immunogenic composition. Various methods of formulation and administration to a patient are described herein, especially wherein the patient suffers from an infectious disease and/or cancer.

4 Claims, 5 Drawing Sheets
Specification includes a Sequence Listing.

(56) References Cited

U.S. PATENT DOCUMENTS

| | | | |
|---|---|---|---|
| 9,943,591 B2* | 4/2018 | Apelian | C12N 7/00 |
| 9,987,352 B2* | 6/2018 | King | A61P 1/16 |
| 10,188,714 B2* | 1/2019 | Franzusoff | A61K 35/17 |
| 10,265,393 B2* | 4/2019 | King | C12N 7/00 |
| 10,363,294 B2* | 7/2019 | Palena | A61P 13/12 |
| 10,441,650 B2* | 10/2019 | Apelian | A61K 45/06 |
| 10,849,971 B2* | 12/2020 | King | A61K 39/12 |
| 11,065,313 B2* | 7/2021 | King | A61K 39/0005 |
| 2002/0044948 A1 | 4/2002 | Samir et al. | |
| 2003/0035810 A1 | 2/2003 | Caplan | |
| 2007/0172503 A1 | 7/2007 | Selitrennikoff et al. | |
| 2007/0224208 A1 | 9/2007 | Guo et al. | |
| 2008/0003239 A1 | 1/2008 | Duke et al. | |
| 2009/0074805 A1 | 3/2009 | Duke et al. | |
| 2009/0098154 A1 | 4/2009 | Franzusoff et al. | |
| 2009/0142366 A1 | 6/2009 | Franzusoff et al. | |
| 2009/0142367 A1 | 6/2009 | Franzusoff et al. | |
| 2009/0304741 A1 | 12/2009 | Duke et al. | |
| 2010/0034840 A1 | 2/2010 | Apelian et al. | |
| 2010/0104604 A1 | 4/2010 | Selitrennikoff et al. | |
| 2010/0111912 A1 | 5/2010 | Apelian et al. | |
| 2010/0150963 A1 | 6/2010 | Duke et al. | |
| 2010/0189749 A1 | 7/2010 | Franzusoff et al. | |
| 2010/0196411 A1 | 8/2010 | Duke et al. | |
| 2010/0215678 A1 | 8/2010 | Guo et al. | |
| 2011/0150909 A1 | 6/2011 | Franzusoff et al. | |
| 2011/0256098 A1 | 10/2011 | Apelian et al. | |
| 2012/0107347 A1 | 5/2012 | Hodge et al. | |
| 2012/0321664 A1 | 12/2012 | Bellgrau et al. | |
| 2016/0271242 A1 | 9/2016 | Sala et al. | |

FOREIGN PATENT DOCUMENTS

| | | |
|---|---|---|
| WO | WO 2007/092792 | 8/2007 |
| WO | WO 2010/065626 | 6/2010 |
| WO | WO 2011/115914 | 9/2011 |
| WO | WO 2012/019127 | 2/2012 |
| WO | WO 2012/083302 | 6/2012 |
| WO | WO 2012/109404 | 8/2012 |
| WO | WO 2012/125998 | 9/2012 |
| WO | WO 2012/174220 | 12/2012 |
| WO | WO 2013/025972 | 2/2013 |
| WO | IVO 2014/160747 | 10/2014 |

OTHER PUBLICATIONS

Brake et al. "alpha-Factor-directed synthesis and secretion of mature foreign proteins in Saccharomyces cerevisiae," Proceedings of the National Academy of Sciences USA, Aug. 1984, vol. 81, pp. 4642-4646.

Bussey et al., "Yeast plasma membrane ghosts. An analysis of proteins by two-dimensional gel electrophoresis," Biochimica et Biophysica Acta, 1979, vol. 553(2), pp. 185-196, abstract only, 1 page.

Chen et al., "A testicular antigen aberrantly expressed in human cancers detected by autologous antibody screening," Proceedings of the National Academy of Sciences USA, 1997, vol. 94, pp. 1914-1918.

Cohen et al., "Nucleotide sequence of the cDNA encoding human tyrosinase-related protein," Nucleic Acids Research, 1990, vol. 18(9), pp. 2807-2808.

Eto et al., "Immunization with recombinant Escherichia coli expressing retinal S-antigen-induced experimental autoimmune uveitis (EAU) in Lewis rats", Cellular Immunology, vol. 147, No. 1 Mar. 1993, pp. 203-214.

Fattal-German et al., "Assessment of the Anti-Viral Effect of a Short-Term Oral Treatment of Mice with Live Saccharomyces Cerevisiae Cells," Developments in Biological Standardization, 1992, vol. 77, pp. 115-120.

Franzusoff et al. "Biochemical and Genetic Definition of the Cellular Protease Required for HIV-1 gp160 Processing," The Journal of Biological Chemistry, Feb. 1995, vol. 270, No. 7, pp. 3154-3159.

Franzusoff et al., "Glucose Transport Activity in Isolated Plasma Membrane Vesicles from Saccharomyces cerevisiae," The Journal of Biological Chemistry, 1983, vol. 258(6), pp. 3608-3614.

Franzusoff et al., "Analysis of Polypeptide Transit through Yeast Secretory Pathway," Methods in Enzymology, 1991, vol. 194, pp. 662-674.

Franzusoff, A. et al. "Yeasts Encoding Tumour Antigens in Cancer Immunotherapy," Expert Opinion on Biological Therapy, Apr. 2005, vol. 5, No. 4, pp. 565-575.

Fujita et al. "Studies in the development of Japanese encephalitis vaccine: expression of virus envelope glycoprotein V3 (E) gene in yeast," Bulletin of the World Health Organization, Feb. 1987, vol. 65, No. 3, pp. 303-308.

GenBank Accession No. M29540, 2 pages.

Hollstein et al., "Database of p53 gene somatic mutations in human tumors and cell lines," Nucleic Acids Research, 1994, vol. 22(17), pp. 3551-3555.

Israeli et al., "Molecular Cloning of a Complementary DNA Encoding a Prostate-specific Membrane Antigen," Cancer Research, 1993, vol. 53, pp. 227-230.

Jackson et al., "A second tyrosinase-related protein, TRP-2, maps to and is mutated at the mouse slaty locus," The EMBO Journal, 1992, vol. 11(2), pp. 527-535.

Jacob et al., "Yeast lysates carrying the nucleoprotein from measles virus vaccine as a novel subunit vaccine platform to deliver Plasmodium circumsporozoite antigen," Malaria Journal, 2017, vol. 16(1), article No. 259, pp. 1-14.

Kawakami et al., "Identification of a human melanoma antigen recognized by tumor-infiltrating lymphocytes associated with in vivo tumor rejection," Proceedings of the National Academy of Sciences USA, 1987, vol. 91, pp. 6458-6462.

Kawakami et al. "Identification of the Immunodominant Peptides of the MART-1 Human Melanoma Antigen Recognized by the Majority of HLA-A2-restricted Tumor Infiltrating Lymphocytes," The Journal of Experimental Medicine, 1994, vol. 180, pp. 347-352.

Klepfer et al., "Characterization of rabies glycoprotein expressed in yeast," Archives of Virology, 1993, vol. 128, pp. 269-286.

Kwon et al., "Isolation and sequence of a cDNA clone for human tyrosinase that maps at the mouse c-albino locus," Proceedings of the National Academy of Sciences USA, 1987, vol. 84, pp. 7473-7477.

Lu, et al., "Mutation-Selective Tumor Remission with Ras-Targeted, Whole Yeast-Based Immunotherapy," Cancer Research, 2004, vol. 64, pp. 5084-5088.

Moore et al., "Introduction of Soluble Protein into the Class I Pathway of Antigen Processing and Presentation," Cell, 1988, vol. 54, pp. 777-785.

Moore et al., "Novel yeast-based vaccine 1-40, against HIV-SF2 gp160 promotes a cytotoxic 43-62 cell response.", FASEB Journal (online), vol. 10. No. 6. 1996, p. A1473, ZP002186594, Joint Meeting of the American Society for Biochemistry and Molecular Biology, the American Society for Investigative Pathology and the American Association of Immunologists; New Orleans, LA, USA; Jun. 2-6, 1996.

O'Hagan, "Recent Advances in Vaccine Adjuvants for Systemic and Mucosal Administration," Journal of Pharmacy and Pharmacology, 1998, vol. 50, pp. 1-10.

Falo et al., "Targeting antigen into the Phagocytic pathway in vivo induces protective tumour immunity," Nature Medicine, 1995, vol. 1(7), pp. 649-653.

Ridge et al., "A conditioned dendritic cell can be a temporal bridge between a CD4+ T-helper and a T-killer cell," Nature, 1998, vol. 393, pp. 474-478.

Rodriguez et al., "Selective transport of internalized antigens to the cytosol for MHC class I presentation in dendritic cells," Nature Cell Biology, 1999, vol. 1, pp. 362-368.

Schreuder et al. "Yeast expressing hepatitis B virus surface antigen determinants on its surface: implications for a possible oral vaccine," Vaccine, Apr. 1996, vol. 14, No. 5, pp. 383-388.

Sinai et al., "Enhancement of Resistance to Infectious Diseases by Oral Administration of Brewer's Yeast," Infection and Immunity, May 1974, vol. 9, No. 5, pp. 781-787.

(56) References Cited

OTHER PUBLICATIONS

Stribling et al., "Aerosol gene delivery in vivo," Proceedings of National Academy of Sciences USA, 1992, vol. 89, pp. 11277-11281.
Brown et al., "Dectin-1 Mediates the Biological Effects of -Glucans," Journal of Experimental Medicine, 2003, vol. 197(9), pp. 1119-1124.
Stubbs, et al., "Whole recombinant yeast vaccine activates dendritic cells and elicits protective cell-mediated immunity," Nature Medicine, 2001 vol. 7(5), pp. 625-629.
Valenzuela et al. "Antigen engineering in yeast: Synthesis and assembly of hybrid hepatitis B surface antigen-Herpes simplex 1 gD particles", Bio/Technology, Apr. 1985, vol. 3, 323-326.
International Search Report and Written Opinion for International (PCT) Patent Application No. PCT/US2019/031962, dated Sep. 20, 2019 15 pages.
Invitation to Pay Additional Fees for International (PCT) Patent Application No. PCT/US2019/031962, dated Jul. 23, 2019 2 pages.
International Report on Patentability for International (PCT) Patent Application No. PCT/US2019/031962, dated Nov. 26, 2020 10 pages.
Extended European Search Report for European Patent Application No. 19804208.7, dated Mar. 3, 2022 11 pages.
Official Action (with English machine translation) for Chinese Patent Application No. 201980032564.4, dated Oct. 20, 2023 10 pages.
Official Action (with English machine translation) for Chinese Patent Application No. 201980032564.4, dated Jun. 28, 2024 17 pages.

\* cited by examiner

LYSATES OF RECOMBINANT YEAST FOR INDUCING CELLULAR IMMUNE RESPONSES

CROSS-REFERENCE TO RELATED APPLICATIONS

This application is a national stage application under 35 U.S.C. 371 and claims the benefit of PCT Application No. PCT/US2019/031962 having an international filing date of 13 May 2019, which designated the United States, and which PCT application claimed the benefit of priority under 35 U.S.C. § 119 (e) to U.S. Provisional Patent Application No. 62/671,587, filed May 15, 2018. The entire contents of each of which are incorporated herein by reference.

REFERENCE TO A SEQUENCE LISTING

This application contains a Sequence Listing submitted electronically as a text file by EFS-Web. The text file, named "3923-59-PCT_ST25", has a size in bytes of 3000 bytes, and was recorded on May 13, 2019. The information contained in the text file is incorporated herein by reference in its entirety pursuant to 37 CFR § 1.52(e)(5).

FIELD OF THE INVENTION

The present invention generally relates to immunotherapeutic compositions, specifically, lysates of recombinant yeast for inducing cellular immune responses and their uses.

BACKGROUND OF THE INVENTION

Vaccines are widely used to prevent disease and to treat established diseases (therapeutic vaccines). There remains, however, an urgent need to develop safe and effective vaccines and adjuvants for a variety of diseases, including those due to infection by pathogenic agents, cancers and other disorders amenable to treatment by elicitation of an immune response.

Protein antigens (e.g. subunit vaccines, the development of which was made possible by recombinant DNA technology), when administered without adjuvants, induce weak humoral (antibody) immunity and have therefore been disappointing to date as they exhibit only limited immunogenicity. An additional disadvantage of subunit vaccines, as well as of killed virus and recombinant live virus vaccines, is that while they appear to stimulate a strong humoral immune response when administered with adjuvants, they fail to elicit protective cellular immunity. Adjuvants are used experimentally to stimulate potent immune responses in mice, and are desirable for use in human vaccines, but few are approved for human use. Indeed, the only adjuvants approved for use in the United States are the aluminum salts, aluminum hydroxide and alu-minum phosphate, neither of which stimulates cell-mediated immunity. Aluminum salt formulations cannot be frozen or lyophilized, and such adjuvants are not effective with all antigens. Moreover, most adjuvants do not lead to induction of cytotoxic T lymphocytes (CTL). CTL are needed to kill cells that are synthesizing aberrant proteins including viral proteins and mutated "self" proteins. Vaccines that stimulate CTL are being intensely studied for use against many viruses (e.g., HIV, HCV, HPV, HSY, CMV, EBY), intracellular bacteria (e.g., tuberculosis); intracellular parasites (e.g., malaria, leishmaniasis, schistosomiasis, leprosy), and all cancers (e.g., melanoma, prostate, ovarian, etc.). Thus, adjuvants are needed that stimulate CTL and cell-mediated immunity in general.

Yeast have been used in the production of subunit protein vaccines, including those tested in the HIV vaccine trials and in hepatitis B vaccine; however, in these cases yeast are used to produce the protein, but the yeast cells or subcellular fractions thereof are not actually delivered to the patient. Yeast have also been fed to animals prior to immunization to try to prime the immune response in a non-specific manner (i.e., to stimulate phagocytosis as well as the production of complement and interferon). The results have been ambiguous, and such protocols have not generated protective cellular immunity; see, for example, Fattal-Ger-man et al., 1992, Dev. Biol. Stand. 77, 115-120; Bizzini et al., 1990, FEMS Microbial. Immunol. 2, 155-167.

U.S. Pat. No. 5,830,463, issued Nov. 3, 1998, to Duke et al. described the use of nonpathogenic yeast carrying at least one compound capable of modulating an immune response, and demonstrated that such complexes are efficacious at stimulating cell-mediated, as well as humoral, immunity. In particular, U.S. Pat. No. 5,830,463 demonstrated that yeast which are genetically engineered to express a heterologous antigen can elicit both a cell-mediated and a humoral immune response when administered to a mammal.

There is currently a need for improved vaccines that stimulate T cells, and particularly cytotoxic T lymphocyte (CTL), mediated immunity against cell-associated or endogenous antigens. Targets for these vaccines include cells infected with viruses, intracellular bacteria and parasites, as well as cancers. The initiation of CTL-mediated immunity requires that antigenic peptides be presented in association with major histocompatibility (MHC) class 1 molecules on the surface of professional antigen presenting cells (APCs) and, in particular, dendritic cells (DCs) (Ridge et al., Nature 393:474-8 1998)). Dendritic cells are the major antigen presenting cells (APCs) for initiation of immune responses. As DCs are unique in their ability to activate naive CD4+ and CD8+ T cells, they play a crucial role in priming both MHC class II- and class I-restricted, antigen-specific T cell responses (Ridge et al., Nature 393:474-8 (1998); Banchereau et al., Nature 392:245-52 (1998)). However, exogenously introduced antigens, for example, those found in vaccines consisting of antigenic proteins or killed pathogens, are predominantly processed via the MHC class II pathway for presentation to CD4+ T cells (Moore et al., Cell 54:777-85 (1988)). These types of vaccines stimulate potent humoral immunity but are relatively ineffective at stimulating CD8+ CTL. This shortcoming has led to an investigation of vaccine strategies that specifically target DCs to present antigens via MHC class I in addition to class II. DCs have been shown to possess a unique pathway for processing exogenous antigen, especially in particulate form, for presentation by the MHC class I pathway (Rodriguez et al., Nat Cell Biol 1:362-368 (1999)). In this regard, various liposome-like, particulate preparations composed of antigenic proteins or peptides with added adjuvants have shown promise at stimulating CTL (Palo et al., Nat Med 1:649-53 (1995); O'Hagan, J Pharm Pharmacol 50:1-10 (1998)). The particulate nature of these immunostimulatory complexes (ISCOMS) allows them to be readily phagocytosed by DCs that are recruited to the site of vaccination and which become activated by the adjuvant moiety.

Dendritic cell-based cancer vaccines are under intense study as well. Dendritic cells are expanded ex vivo and "loaded" with peptides (derived from suspected tumor antigens) or mixed with the patient's cancer cells (DCs phagocytose the cells and present tumor antigens). However, peptide loading is inefficient and requires knowledge of the particular peptide being used. Phagocytosis of dead tumor cells and debris leads to class II MHC presentation but not class I MHC presentation which is needed for activation of CTL. Therefore, there is a need in the art for improved vaccines, including improved DC vaccines.

Whole recombinant yeast-based therapeutic vaccines (i.e., Tarmogens) elicit CD4+, CD8+ and Th17 T cell responses that are capable of eliminating cancer cells and cells infected with microorganisms in man. A Tarmogen® (TARgeted MOlecular immunoGEN, GlobeImmune, Inc., Louisville, Colorado) generally refers to a yeast vehicle expressing one or more heterologous antigens extracellularly (on its surface), intracellularly (internally or cytosolically) or both extracellularly and intracellularly. Tarmogens have been generally described in the art. See, e.g., U.S. Pat. No. 5,830,463. Responses to standalone/single agent Tarmogen have been shown to induce a survival benefit in several different animal models. In humans, signs of such benefits have been observed in clinical trials with pancreatic cancer patients and in chronic hepatitis C patients although as yet, statistical significance of primary endpoint readouts has not been reached with the exception of biomarker-selected patient subsets. Further trials featuring these whole recombinant yeast-based therapeutic vaccines combined with other immune modulating agents are underway and may enhance clinical efficacy. An increase in the magnitude of these Tarmogen-emergent immune responses, especially cytotoxic T cell (CTLs), may result in more effective target cell clearance, leading to efficacy in a greater percentage of patients.

In the 1990's, yeast-based immunotherapy compositions were introduced as novel compositions for inducing immune responses through both the MHC class I-restricted and the MHC class II-restricted pathways of antigen-presenting cells (see U.S. Pat. No. 5,830,463). Although these compositions are initially exposed to the immune system as an exogenous antigen(s), yeast-based immunotherapy compositions are uniquely able to trigger the induction of both a CD8+ cytotoxic T cell response through cross-presentation of antigens by the MHC class I-restricted pathway, as well as a CD4+ T cell response through presentation of antigens by the MHC class II-restricted pathway (See, e.g., U.S. Pat. Nos. 5,830,463 and 7,083,787, Stubbs et al., Nat. Med. 7:625-629 (2001) and Lu et al., Cancer Research 64:5084-5088 (2004)). Yeast-based immunotherapy compositions stimulate pattern recognition receptors (PRR); upregulate adhesion molecules, costimulatory molecules, and MHC class I and class II molecules on antigen presenting cells including DCs; and induce the production of proinflammatory cytokines by antigen presenting cells (e.g., TNF-α and IL-12) (see, e.g., Stubbs et al., supra; Brown et al., *J Exp. Med.* 197:1119-1124 (2003)).

In the context of yeast-based immunotherapeutic compositions, which may be engineered to express one or more antigens, the complexities of the mechanism of action of yeast-based immunotherapeutics with respect to the immune system and therapeutic efficacy have not yet been fully identified. It is desirable to better understand how different individuals respond to immunization with yeast-based immunotherapy compositions, and thereby be able to manipulate and personalize immunotherapeutic strategies to more effectively elicit a desired immune response that is most appropriate for a given disease or condition in an individual.

SUMMARY OF THE INVENTION

Various embodiments of the invention are described below. However, the invention is not limited to embodiments described in this summary, as inventions described in the description that follows are also expressly encompassed.

One embodiment of the invention relates to an immunogenic composition, comprising (a) a yeast lysate prepared from a yeast, wherein the lysate lacks yeast membranes and yeast cell walls; and (b) at least one antigen that is heterologous to the yeast.

Another embodiment of the invention relates an immunogenic preparation, comprising (a) a first immunogenic composition, comprising (i) a yeast lysate prepared from a yeast, wherein the lysate lacks yeast membranes and yeast cell walls; and (ii) at least one antigen that is heterologous to the yeast; and (b) a second immunogenic composition, comprising (i) a yeast vehicle selected from the group consisting of: a whole yeast, a yeast spheroplast, a yeast cytoplast, a yeast ghost, and a subcellular yeast particle; and (ii) at least one antigen that is heterologous to the yeast. In one aspect of this embodiment, the first immunogenic composition and the second immunogenic compositions are combined in a ratio of about 90:10 to about 10:90.

Yet another embodiment of the invention relates to a method to produce an immunogenic composition, comprising (a) lysing yeast cells; and (b) removing cell walls and cell membranes from the lysed cells, wherein the lysed cells comprise an antigen that is heterologous to the yeast. In one aspect of this embodiment, the step of lysing is performed by a method selected from the group consisting of glass bead rupture, high pressure homogenization, ultrasonication, electrical lysis, physical lysis, chemical lysis, and enzymatic lysis. In yet another aspect of this embodiment, the step of removing is performed by a method selected from the group consisting of centrifugation, filtration and affinity chromatography. In one aspect, the immunogenic composition and the yeast vehicle are combined in a ratio of about 90:10 to about 10:90 yeast unit equivalents. In another aspect, prior to the step of removing the cell walls and cell membranes the lysed yeast cells are further treated by ultrasonication to release the antigen from the cell walls and cell membranes.

Another embodiment of the invention relates to a method to elicit a cytotoxic T cell immune response in a subject, the method comprising administering to the subject an immunogenic composition comprising (a) a yeast lysate prepared from a yeast, wherein the lysate lacks yeast membranes and yeast cell walls; and (b) at least one antigen that is heterologous to the yeast.

In one aspect of this embodiment, the method further comprises combining the immunogenic composition with a composition comprising a whole recombinant, inactivated yeast vehicle and at least one antigen that is heterologous to the yeast.

In one aspect of this embodiment, the subject is administered the immunogenic composition by an administration route selected from the group consisting of intravenous, intraperitoneal, subcutaneous, intradermal, intranodal, intramuscular, transdermal, inhaled, intranasal, oral, intraocular, intraarticular, intracranial, and intraspinal.

In one aspect of this embodiment, the immunogenic composition is formulated in a pharmaceutically acceptable excipient suitable for administration by injection of a subject.

In one aspect of this embodiment, the subject is administered the immunogenic composition in a dose from about 0.1 Y.U. to about 100 Y.U.

In one aspect of this embodiment, the subject is administered the immunogenic composition in a dose from about 10 Y.U. to about 80 Y.U.

In one aspect of this embodiment, the immunogenic composition is administered weekly.

In one aspect of this embodiment, the immunogenic composition is administered every other week.

In one aspect of this embodiment, the immunogenic composition is administered monthly.

In one aspect of this embodiment, the composition comprises multiple antigens.

Still another embodiment of the invention relates to a method to elicit an antigen-specific humoral immune response and an antigen-specific cell-mediated immune response in a subject, said method comprising administering to the subject an immunogenic composition comprising (a) a yeast lysate prepared from a yeast, wherein the lysate lacks yeast membranes and yeast cell walls; and (b) at least one antigen that is heterologous to the yeast.

In one aspect of this embodiment, the method further comprising administering to the subject a whole recombinant, inactivated yeast combined with at least one antigen that was expressed by the yeast.

In one aspect of this embodiment, the subject is administered the immunogenic composition by an administration route selected from the group consisting of intravenous, intraperitoneal, subcutaneous, intradermal, intranodal, intramuscular, transdermal, inhaled, intranasal, oral, intraocular, intraarticular, intracranial, and intraspinal.

In one aspect of this embodiment, the immunogenic composition is formulated in a pharmaceutically acceptable excipient suitable for administration by injection of a subject.

In one aspect of this embodiment, the subject is administered the immunogenic composition in a dose from about 0.1 Y.U. to about 100 Y.U.

In one aspect of this embodiment, the subject is administered the immunogenic composition in a dose from about 10 Y.U. to about 80 Y.U.

In one aspect of this embodiment, the immunogenic composition is administered weekly.

In one aspect of this embodiment, the immunogenic composition is administered every other week.

In one aspect of this embodiment, the immunogenic composition is administered monthly.

In one aspect of this embodiment, the composition comprises multiple antigens.

In one aspect of any embodiment of the invention described above, the antigen was expressed by the yeast.

In any of the embodiments described herein, in one aspect, the antigen is added to the yeast lysate.

In any of the embodiments described herein, in one aspect, the antigen is selected from the group consisting of viral antigens, mammalian cell surface molecules, bacterial antigens, fungal antigens, protozoan antigens, helminth antigens, ectoparasite antigens, cancer antigens and tumor neoantigens.

In any of the embodiments described herein, in one aspect, the heterologous antigen is expressed by the yeast before the yeast is lysed.

In any of the embodiments described herein, in one aspect, the heterologous antigen is added to the lysed yeast.

In any of the embodiments described herein, in one aspect, further comprising combining the immunogenic composition with at least one antigen that is expressed by a whole recombinant, inactivated yeast vehicle.

In any of the embodiments described herein, in one aspect, the yeast vehicle is a heat inactivated yeast cell.

In any of the embodiments described herein, in one aspect, the yeast are from *Saccharomyces*.

In any of the embodiments described herein, in one aspect, the yeast are from *Saccharomyces cerevisiae*.

DETAILED DESCRIPTION OF THE INVENTION

Figure 1:
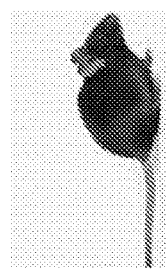
FIG. 1 is a schematic of an in vivo CTL assay.
Figure 1:
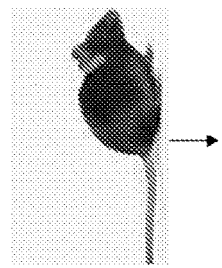
Figure 1:
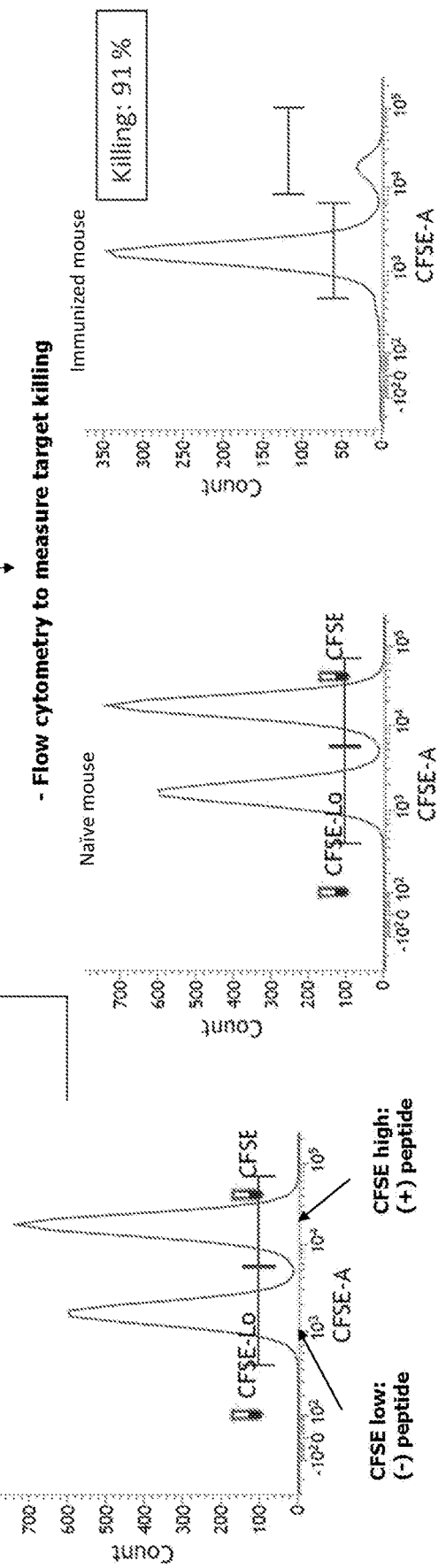

The present invention is directed to methods of making and using lysates of yeast that are clear of yeast membranes and yeast cell walls ("yeast lysate" or "YL"), alone or in combination with intact yeast-based immunotherapeutic compositions as a means to increase the magnitude of disease antigen-specific CTL responses compared to intact immunotherapeutic compositions alone. Without intending to be bound by theory, the rationale for increased response is that faster/more efficient disease antigen availability to antigen presenting cells (APCs) and/or exposure of APCs to double stranded RNA and DNA or other cellular factors derived from the yeast cytoplasm can result in improved antigen presentation to T cells via more efficient MEW loading and stronger APC activation. The latter can occur through (for example) activation of Toll like receptors (TLRs) 3 and 9 that are not efficiently activated by intact Tarmogen alone.

As provided in the Examples herein, YL was tested in murine in vivo CTL assays and compared against an intact yeast-based immunotherapeutic, namely, a Tarmogen, alone (T). The results showed that YL dramatically improved the magnitude of antigen-specific in vivo cytolytic activity as compared to T in two experiments for 5 different Tarmogen vaccine candidates. In these experiments, T elicited from 0 to about 20% killing, whereas YL consistently elicited up to about an 80 to 95% killing.

The invention results in a dramatic improvement in CTL activity over intact Tarmogen alone in a mouse in vivo CTL model, using yeast-expressed ovalbumin antigen as well as certain yeast-expressed polyepitope antigens as test cases. The results are shown in Example 1 and FIGS. 1 and 2. This improved CTL activity can translate to a pronounced benefit in human clinical trials for infectious disease and cancer.

In the third example presented herein, YLs were compared to intact yeast in the ability to generate antigen-specific CD4+ T cell responses using intracellular cytokine staining. Mice were vaccinated intradermally with a intact vs. lysed "I-A$^b$-cyto" yeast that express a polyepitope (a concatemer of class II T cell neoepitopes) on days 0 and 38. Nine days after the second immunization, spleens were removed and stimulated with a pool of class II MHC binding peptides matched to the vaccine and the magnitude of "recall" (re-activated) CD4+ T cell response was measured using ICS coupled to a flow cytometry readout. The results showed that I-A$^b$-cyto YL immunization generated 6-fold more neoepitope-specific, CD4+ T cells producing IFNγ and TNFα than the intact yeast elicited (0.059% TNFα+/IFNγ+ CD4 T cells for YL vs. 0.01% for the intact yeast, FIG. 3).

In the fourth example presented herein, YLs were compared to intact yeast in their ability to generate antigen-specific CD8+ T cell responses, again using intracellular cytokine staining. Mice were vaccinated intravenously with intact vs. lysed yeast that express a polyepitope (a concatemer of class I T cell neoepitopes fused to a the positive control epitope SIINFEKL (SEQ ID NO:9). This Tarmogen is called "93" (so named for the size of the polyepitope, 93 kDa) and it contains a different arrangement and number of neoepitopes than the variants used in the examples above. Immunizations were conducted on days 0 and 38, and nine days after the second immunization, spleens were removed and the splenocyte preparations were stimulated with either no antigen (DMSO peptide solvent in growth medium only=mock) or SIINFEKL (SEQ ID NO:9) peptide, which is a dominant murine class I MHC-binding epitope). The magnitude of the SIINFEKL (SEQ ID NO:9)-specific recall CD8+ T cell response was measured using ICS followed by analysis with flow cytometry. The results showed that YL immunization generated 20-fold more neoepitope-specific, CD8+ T cells producing IFNγ and TNFα than the intact yeast did (0.45% TNFα+IFNγ+CD8 T cells for YL immunization vs. 0.022% for mock, FIG. 4).

Figure 5:
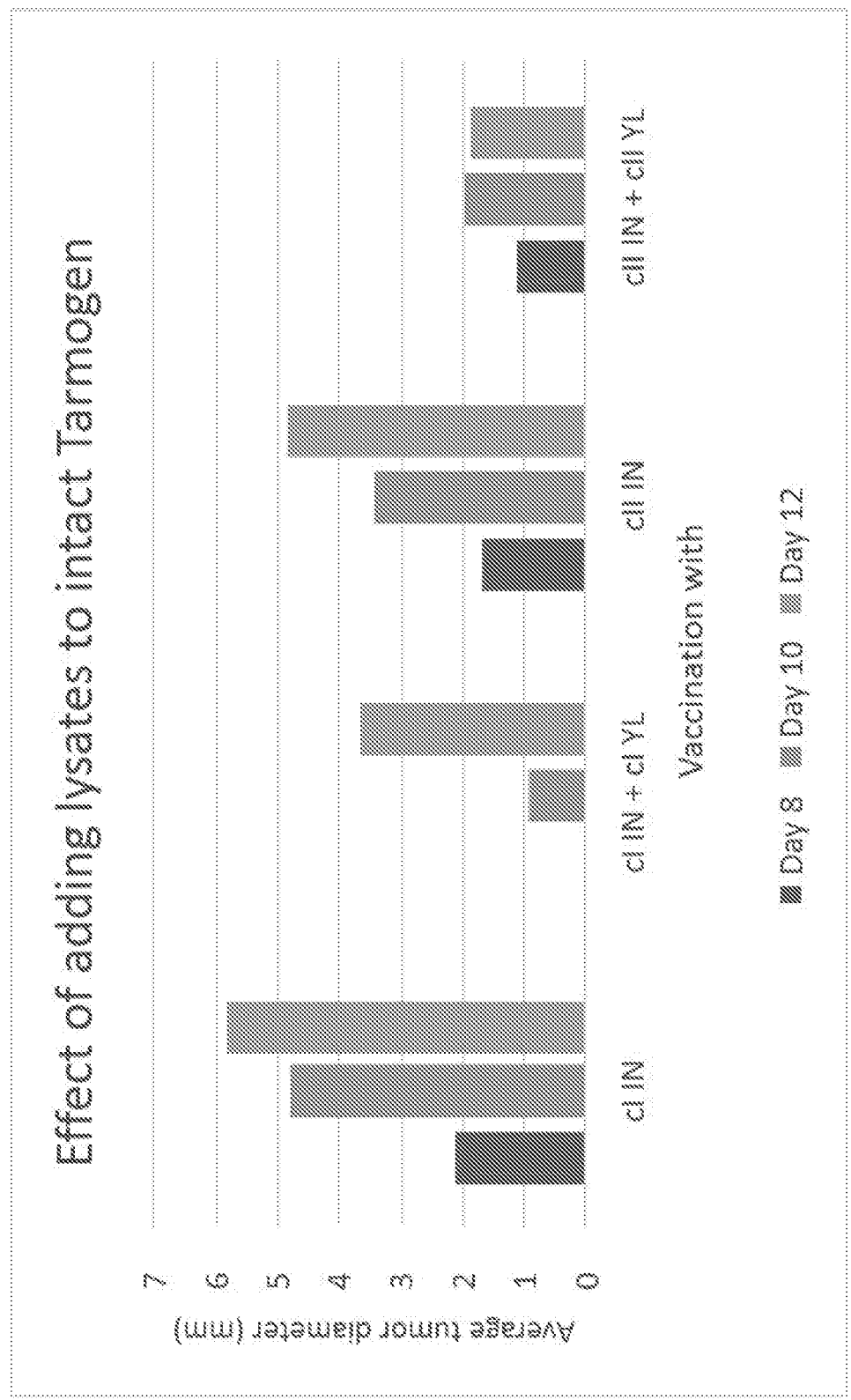
FIG. 5 shows the effects of adding lysates to intact Tramogen. cI IN, intact yeast expressing a fusion of class I neoepitopes; cII IN, intact yeast expressing a fusion of class II neoepitopes; cI IN+cI YL, 1.25 YU of cI IN mixed with 1.25 YU of cI YL; cII IN+cII CL, 1.25 YU of cII IN mixed with 1.25 YU of cII YL. Days, number of days post-tumor challenge. Day 8 is first bar in set (except for cI IN+Ci YL which has no Day 8 data shown), Day 10 is middle bar in set (except for cI IN+Ci YL which has Day 10 as the first bar); Day 12 is last bar in set.

In the fifth example presented herein, YLs of polyepitope yeast K$^b$-cyto ("cI") and I-A$^b$-cyto ("cII") were added to the intact tarmogen (expressing the same/matched polyepitope) in equal parts (1:1) to determine if the YLs (CLs) could improve the extent of tumor protection that is provided by intact yeast. Briefly, mice were immunized three times (once per week) with intact yeast ("cI IN" or "cII IN", 5 YU total) OR 2.5 intact yeast mixed with 2.5 YU of YL (e.g., cI IN+cI CL). The concept here is that vaccination should mount neoepitope-targeted T cell responses that can kill or otherwise inhibit growth of subcutaneously implanted B16F10 tumors in vivo. Vaccination was done in 4 different mouse groups, to test class I polyepitope yeast and class II polyepitope yeast individually or combined (FIG. 5). One week after the 3$^{rd}$ immunization, mice were challenged with the aggressive B16F10 tumor line expressing neoepitopes matched to those contained in the yeast vaccines, and tumor growth was measured every other day through day 12 post-challenge. The results showed that intact yeast mixed with YL slowed the growth of tumors 2- to 5 fold as compared to intact yeast alone (compare for example the day 10 time point for "cI IN+cI CL" against the same time point for "cI IN" alone.) The total amount of yeast material used for immunization was the same in these groups, while tumor growth inhibition was up to 5-fold higher for groups containing CLs (FIG. 5.)

YL is thought to work differently from any other known vaccine because of its ability to elicit activation of not only TLR 2, 4, and 6 (intact yeast), but also of TLR 3 (activated by dsRNA in the lysate) and TLR 9 (activated by dsDNA in the lysate). Other receptors that will be engaged by the YL mixture include Dectin-1 and the mannose receptor (Haller et al), by the intact Tarmogen component. This broad activation can lead to potent and full APC activation via multiple cellular pathways. Additionally, the presence of the intact Tarmogen in the mixture ensures that phagocytosis will occur by APCs, followed by antigen cross-presentation concomitant with APC maturation. The heterologous antigen and other cellular components in the lysates including DNA and RNA/RNPs will accompany the intact yeast into the phagosomes, inducing multiple activation pathways in the process.

One embodiment of the invention relates to an immunogenic composition, comprising (a) a yeast lysate prepared from a yeast, wherein the lysate lacks yeast membranes and yeast cell walls; and (b) at least one antigen that is heterologous to the yeast.

Another embodiment of the invention relates to an immunogenic preparation, comprising (a) a first immunogenic composition, comprising (i) a yeast lysate prepared from a yeast, wherein the lysate lacks yeast membranes and yeast cell walls; and (ii) at least one antigen that is heterologous to the yeast; and (b) a second immunogenic composition, comprising (i) a yeast vehicle selected from the group consisting of: a whole yeast, a yeast spheroplast, a yeast cytoplast, a yeast ghost, and a subcellular yeast particle; and (ii) at least one antigen that is heterologous to the yeast. In one aspect of this embodiment, the first immunogenic composition and the second immunogenic compositions are combined in a ratio of about 90:10, about 80:20, about 70:30, about 60:40, about 50:50, about 40:60, about 30:70, about 20:80 or about 10:90. In a preferred embodiment, the ratio is about 50:50. Alternative embodiments include the first and second immunogenic compositions in ranges of using any of the foregoing ratios as end points (e.g., 90:10 to 10:90 or 80:20 to 30:70). In still another aspect, the percentage of the first immunogenic composition in the combined composition is about 99%, about 95%, about 90%, about 80%, about 70%, about 60%, about 50%, about 40%, about 30%, about 20% or about 10%, or any whole number percentage between 10% and 99%. Percentages are based on yeast units.

Yet another embodiment of the invention relates to a method to produce an immunogenic composition, comprising (a) lysing yeast cells; and (b) removing cell walls and cell membranes from the lysed cells, wherein the lysed cells comprise an antigen that is heterologous to the yeast. In one aspect of this embodiment, the step of lysing is performed by a method selected from the group consisting of glass bead rupture, high pressure homogenization, ultrasonication, electrical lysis, physical lysis, chemical lysis, and enzymatic lysis. In yet another aspect of this embodiment, the step of removing cell walls and membranes is performed by a method selected from the group consisting of centrifugation, filtration and affinity chromatography. In one aspect, the immunogenic composition is combined with a whole recombinant, inactivated yeast vehicle comprising at least one antigen that is heterologous to the whole recombinant inactivated yeast. In this embodiment, the composition and the yeast vehicle can be combined in a ratio of about 90:10, about 80:20, about 70:30, about 60:40, about 50:50, about 40:60, about 30:70, about 20:80 or about 10:90 yeast unit equivalents.

Another embodiment of the invention relates to a method to elicit a cytotoxic T cell immune response in a subject, the method comprising administering to the subject an immunogenic composition comprising (a) a yeast lysate prepared from a yeast, wherein the lysate lacks yeast membranes and yeast cell walls; and (b) at least one antigen that is heterologous to the yeast. The method can further comprise administering to the subject a whole recombinant, inactivated yeast combined with at least one antigen that was expressed by the yeast.

Still another embodiment of the invention relates to a method to elicit an antigen-specific humoral immune response and an antigen-specific cell-mediated immune response in a subject, said method comprising administering to the subject an immunogenic composition comprising (a) a yeast lysate prepared from a yeast, wherein the lysate lacks yeast membranes and yeast cell walls; and (b) at least one antigen that is heterologous to the yeast. The method can further comprise administering to the subject a whole recombinant, inactivated yeast combined with at least one antigen that was expressed by the yeast.

Immunogenic compositions of the present invention include a yeast lysate prepared from a yeast, wherein the lysate lacks yeast membranes and yeast cell walls. Such a yeast lysate is prepared from yeast that have been lysed, i.e., yeast in which the cell walls and membranes have been disrupted, exposing the yeast cell contents to the rest of the composition. The yeast lysates can be prepared from inactivated, such as heat inactivated, yeast or from live yeast. The yeast can contain a disease-related antigen expressed inside the yeast from a plasmid or from an integrated chromosomal allele. For example, yeast can be lysed by glass bead rupture, such as by mixing with PBS and 500 μL of acid washed 0.2 μm glass beads in a 1.5 mL total volume and vigorously shaking the mixture in a mechanical agitation machine until the cells are ruptured, such as >97% of the cells being ruptured. Alternatively, yeast can be lysed by other methods including high pressure homogenization, ultrasonication, and electrical, physical, chemical and enzymatic techniques. In preferred embodiments, at least about 80% of the cells are ruptured, at least about 85%, at least about 90%, at least about 91%, at least about 92%, at least about 93%, at least about 94%, at least about 95%, at least about 96%, at least about 97%, at least about 98%, at least about 99%.

Preferred genera of yeast strains for production of yeast lysate include *Saccharomyces, Candida, Cryptococcus, Hansenula, Kluyveromyces, Pichia, Rhodotorula, Schizosaccharomyces* and *Yarrowia*, with *Saccharomyces, Candida, Hansenula, Pichia* and *Schizosaccharomyces* being more preferred, and with *Saccharomyces* being particularly preferred. Preferred species of yeast strains include *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe*, and *Yarrowia lipolytica*.

The lysed yeast cell compositions are then further treated to remove yeast membranes and yeast cell walls by any suitable method to produce a yeast lysate lacking yeast membranes and yeast cell walls. For example, yeast membranes and yeast cell walls can be removed from lysed yeast by centrifugation to produce a lysate (supernatant), which is free of cell walls and membranes, such as by centrifugation of lysed yeast for 5 minutes at 16,000 rpm, 25° C. Alternatively, lysates can be cleared of cell wall and membranous debris after rupture by means other than centrifugation. For example, filtration or treatment of cells with conA beads are alternate methods. It will be recognized that while the invention is described are removing yeast membranes and yeast cell walls or reference is made to a lysate lacking yeast membranes and yeast cell walls, suitable processes for removal of materials may not remove 100% of the yeast membranes and yeast cell walls from a lysate. In some embodiments, at least about 80% of the yeast membranes and/or yeast cell walls are removed, at least about 85%, at least about 90%, at least about 91%, at least about 92%, at least about 93%, at least about 94%, at least about 95%, at least about 96%, at least about 97%, at least about 98%, at least about 99%.

Immunogenic compositions of the present invention, in addition to a yeast lysate lacking yeast membranes and yeast cell walls, comprise at least one antigen (which term includes immunogenic domains of antigens) that is heterologous to the yeast. The heterologous antigen can have been expressed by the yeast prior to lysing or the antigen can have been combined with the yeast either before or after lysing and before or after removal of yeast membranes and yeast cell walls from a lysate. In some embodiments, the antigen is provided as a fusion protein, which can include two or more antigens. In one aspect, the fusion protein can include two or more immunogenic domains of one or more antigens, or two or more epitopes of one or more antigens.

The present invention includes the use of at least one "yeast-based immunotherapeutic composition" (which phrase may be used interchangeably with "yeast-based immunotherapy product", "yeast-based immunotherapeutic composition", "yeast-based composition", "yeast-based immunotherapeutic" or "yeast-based vaccine") which can be a yeast lysate that lacks yeast membranes and yeast cell walls, alone or in combination with an intact yeast-based immunotherapeutic composition, such as a Tarmogen. Yeast-based immunotherapeutic compositions elicit an immune response sufficient to achieve at least one therapeutic benefit in a subject. More particularly, a yeast-based immunotherapeutic composition is a composition that includes a YL component, alone or in combination with an intact yeast-based immunotherapeutic composition and can elicit or induce an immune response, such as a cellular immune response, including without limitation a T cell-mediated cellular immune response. In one aspect, the yeast-based immunotherapeutic composition useful in the invention is capable of inducing a CD8+ and/or a CD4+ T cell-mediated immune response and in one aspect, a CD8+ and a CD4+ T cell-mediated immune response. Optionally, a yeast-based immunotherapeutic composition is capable of eliciting a humoral immune response. A yeast-based immunotherapeutic composition useful in the present invention can, for example, elicit an immune response in an individual such that the individual is treated for the disease or condition, or from symptoms resulting from the disease or condition.

Yeast-based immunotherapeutic compositions of the invention may be either "prophylactic" or "therapeutic". When provided prophylactically, the immunotherapeutic compositions of the present invention are provided in advance of any symptom of a disease or condition. The prophylactic administration of the immunotherapeutic compositions serves to prevent or ameliorate or delay time to onset of any subsequent disease. When provided therapeutically, the immunotherapeutic compositions are provided at or after the onset of a symptom of disease. The term, "disease" refers to any deviation from the normal health of an animal and includes a state when disease symptoms are present, as well as conditions in which a deviation (e.g., tumor growth, infection, etc.) has occurred, but symptoms are not yet manifested.

In one embodiment, yeast lysates of the present invention are made from intact yeast-based immunotherapy compositions. In addition, such intact yeast-based immunotherapy compositions can be combined with a yeast lysate-based composition in the present invention. Such intact yeast-based immunotherapy compositions generally comprise a yeast vehicle and an antigen heterologous to the yeast.

Such intact yeast-based immunotherapy compositions, and methods of making and generally using the same, are described in detail, for example, in U.S. Pat. Nos. 5,830,463, 7,083,787, 7,465,454, U.S. Patent Publication 2007-0224208, U.S. Patent Publication No. US 2008-0003239, and in Stubbs et al., Nat. Med. 7:625-629 (2001), Lu et al., Cancer Research 64:5084-5088 (2004), and in Bernstein et al., Vaccine 2008 Jan. 24; 26(4):509-21, each of which is incorporated herein by reference in its entirety. These yeast-based immunotherapeutic products have been shown to elicit immune responses, including cellular and humoral immune responses. Yeast-based immunotherapeutic products are capable of killing target cells expressing a variety of antigens in vivo, in a variety of animal species, and to do so via antigen-specific, CD4+ and CD8+ mediated immune responses. Additional studies have shown that yeast are avidly phagocytosed by and directly activate dendritic cells which then present yeast-associated proteins to CD4+ and CD8+ T cells in a highly efficient manner. See, e.g., Stubbs et al. Nature Med. 5:625-629 (2001) and U.S. Pat. No. 7,083,787.

In any of the yeast-based immunotherapy compositions used in the present invention, the following aspects related to the yeast vehicle are included in the invention. According to the present invention, a yeast vehicle is any yeast cell (e.g., a whole or intact cell) or a derivative thereof (see below) that can be used in conjunction with one or more antigens, immunogenic domains thereof or epitopes thereof in a therapeutic composition of the invention. The yeast vehicle can therefore include, but is not limited to, a live intact yeast microorganism (i.e., a yeast cell having all its components including a cell wall), a killed (dead) or inactivated intact yeast microorganism, or derivatives thereof including: a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), a subcellular yeast membrane extract or fraction thereof (also referred to as a yeast membrane particle and previously as a subcellular yeast particle), any other yeast particle, or a yeast cell wall preparation.

Yeast spheroplasts are typically produced by enzymatic digestion of the yeast cell wall. Such a method is described, for example, in Franzusoff et al., 1991, Meth. Enzymol. 194, 662-674, incorporated herein by reference in its entirety.

Yeast cytoplasts are typically produced by enucleation of yeast cells. Such a method is described, for example, in Coon, 1978, Natl. Cancer Inst. Monogr. 48, 45-55 incorporated herein by reference in its entirety.

Yeast ghosts are typically produced by resealing a permeabilized or lysed cell and can, but need not, contain at least some of the organelles of that cell. Such a method is described, for example, in Franzusoff et al., 1983, J. Biol. Chem. 258, 3608-3614 and Bussey et al., 1979, Biochim. Biophys. Acta 553, 185-196, each of which is incorporated herein by reference in its entirety.

A yeast membrane particle (subcellular yeast membrane extract or fraction thereof) refers to a yeast membrane that lacks a natural nucleus or cytoplasm. The particle can be of any size, including sizes ranging from the size of a natural yeast membrane to microparticles produced by sonication or other membrane disruption methods known to those skilled in the art, followed by resealing. A method for producing subcellular yeast membrane extracts is described, for example, in Franzusoff et al., 1991, Meth. Enzymol. 194, 662-674. One may also use fractions of yeast membrane particles that contain yeast membrane portions and, when the antigen or other protein was expressed recombinantly by the yeast prior to preparation of the yeast membrane particles, the antigen or other protein of interest. Antigens or other proteins of interest can be carried inside the membrane, on either surface of the membrane, or combinations thereof (i.e., the protein can be both inside and outside the membrane and/or spanning the membrane of the yeast membrane particle). In one embodiment, a yeast membrane particle is a recombinant yeast membrane particle that can be an intact, disrupted, or disrupted and resealed yeast membrane that includes at least one desired antigen or other protein of interest on the surface of the membrane or at least partially embedded within the membrane.

An example of a yeast cell wall preparation is isolated yeast cell walls carrying an antigen on its surface or at least partially embedded within the cell wall such that the yeast cell wall preparation, when administered to an animal, stimulates a desired immune response against a disease target.

Any yeast strain can be used to produce a yeast vehicle (either for production of a yeast lysate or to be used in combination with a yeast lysate). Yeast are unicellular microorganisms that belong to one of three classes: Ascomycetes, Basidiomycetes and Fungi Imperfecti. One consideration for the selection of a type of yeast for use as an immune modulator is the pathogenicity of the yeast. In one embodiment, the yeast is a non-pathogenic strain such as *Saccharomyces cerevisiae*. The selection of a non-pathogenic yeast strain minimizes any adverse effects to the individual to whom the yeast vehicle is administered. However, pathogenic yeast may be used if the pathogenicity of the yeast can be negated by any means known to one of skill in the art (e.g., mutant strains). In accordance with one aspect of the present invention, nonpathogenic yeast strains are used.

Genera of yeast strains that may be used in the invention include but are not limited to *Saccharomyces, Candida* (which can be pathogenic), *Cryptococcus, Hansenula, Kluyveromyces, Pichia, Rhodotorula, Schizosaccharomyces* and *Yarrowia*. In one aspect, yeast genera are selected from *Saccharomyces, Candida, Hansenula, Pichia* or *Schizosaccharomyces*, and in one aspect, *Saccharomyces* is used. Species of yeast strains that may be used in the invention include but are not limited to *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe*, and *Yarrowia lipolytica*. It is to be appreciated that a number of these species include a variety of subspecies, types, subtypes, etc. that are intended to be included within the aforementioned species. In one aspect, yeast species used in the invention include *S. cerevisiae, C. albicans, H. polymorpha, P. pastoris* and *S. pombe. S. cerevisiae* is useful due to it being relatively easy to manipulate and being "Generally Recognized As Safe" or "GRAS" for use as food additives (GRAS, FDA proposed Rule 62FR18938, Apr. 17, 1997). One embodiment of the present invention is a yeast strain that is capable of replicating plasmids to a particularly high copy number, such as a *S. cerevisiae* cir$^o$ strain. The *S. cerevisiae* strain is one such strain that is capable of supporting expression vectors that allow one or more target antigen(s) and/or antigen fusion protein(s) and/or other proteins to be expressed at high levels. In addition, any mutant yeast strains can be used in the present invention, including those that exhibit reduced post-translational modifications of expressed target antigens or other proteins, such as mutations in the enzymes that extend N-linked glycosylation.

In one embodiment, a yeast vehicle of the present invention is capable of fusing with the cell type to which the yeast vehicle and antigen/agent is being delivered, such as a dendritic cell or macrophage, thereby effecting particularly efficient delivery of the yeast vehicle, and in many embodiments, the antigen(s) or other agent, to the cell type. As used herein, fusion of a yeast vehicle with a targeted cell type refers to the ability of the yeast cell membrane, or particle thereof, to fuse with the membrane of the targeted cell type (e.g., dendritic cell or macrophage), leading to syncytia formation. As used herein, a syncytium is a multinucleate mass of protoplasm produced by the merging of cells. A number of viral surface proteins (including those of immunodeficiency viruses such as HIV, influenza virus, poliovirus and adenovirus) and other fusogens (such as those involved in fusions between eggs and sperm) have been shown to be able to effect fusion between two membranes (i.e., between viral and mammalian cell membranes or between mammalian cell membranes). For example, a yeast vehicle that produces an HIV gp120/gp41 heterologous antigen on its surface is capable of fusing with a CD4+T-lymphocyte. It is noted, however, that incorporation of a targeting moiety into the yeast vehicle, while it may be desirable under some circumstances, is not necessary. In the case of yeast vehicles that express antigens extracellularly, this can be a further advantage of the yeast vehicles of the present invention. In general, yeast vehicles useful in the present invention are readily taken up by dendritic cells (as well as other cells, such as macrophages).

Immunogenic compositions of the present invention comprise at least one antigen that is heterologous to the yeast from which the composition is formed. The antigen in either a YL or an intact immunotherapeutic composition can have been expressed by the yeast (in the case of a YL, prior to being lysed) or can be added to the immunotherapeutic composition. The antigen(s) can be viral antigens, mammalian proteins, mammalian cell surface molecules, bacterial antigens, fungal antigens, protozoan antigens, helminth antigens, ectoparasite antigens, and cancer antigens.

According to the present invention, the general use herein of the term "antigen" refers: to any portion of a protein (peptide, partial protein, full-length protein), wherein the protein is naturally occurring or synthetically derived, to a cellular composition (whole cell, cell lysate or disrupted cells), to a microorganism or cells (whole microorganism, lysate or disrupted cells) or to a carbohydrate, or other molecule, or a portion thereof. An antigen may, in some embodiments, elicit an antigen-specific immune response (e.g., a humoral and/or a cell-mediated immune response) against the same or similar antigens that are encountered by an element of the immune system (e.g., T cells, antibodies). The term "cancer antigen" can be used interchangeably herein with the terms "tumor-specific antigen", "tumor-associated antigen", "cancer-associated target" or "tumor-associated target" or "neoantigen".

An antigen can be as small as a single epitope, or larger, and can include multiple epitopes. As such, the size of an antigen can be as small as about 5-16 amino acids (e.g., a small peptide) and as large as: a domain of a protein, a partial protein (peptide or polypeptide), a full length protein, including a multimer and fusion protein, chimeric protein, or agonist protein or peptide. In addition, antigens can include carbohydrates.

When referring to stimulation of an immune response, the term "immunogen" is a subset of the term "antigen", and therefore, in some instances, can be used interchangeably with the term "antigen". An immunogen, as used herein, describes an antigen which elicits a humoral and/or cell-mediated immune response (i.e., is immunogenic), such that administration of the immunogen to an individual in the appropriate context (e.g., as part of a yeast-based immunotherapy composition) elicits or induces an antigen-specific immune response against the same or similar antigens that are encountered by the immune system of the individual.

An "immunogenic domain" of a given antigen can be any portion, fragment or epitope of an antigen (e.g., a peptide fragment or subunit or an antibody epitope or other conformational epitope) that contains at least one epitope that acts as an immunogen when administered to an animal. For example, a single protein can contain multiple different immunogenic domains. Immunogenic domains need not be linear sequences within a protein, such as in the case of a humoral immune response.

An epitope is defined herein as a single immunogenic site within a given antigen that is sufficient to elicit an immune response. Those of skill in the art will recognize that T cell epitopes are different in size and composition from B cell epitopes, and that epitopes presented through the Class I MHC pathway differ from epitopes presented through the Class II MHC pathway. Epitopes can be linear sequence or conformational epitopes (conserved binding regions).

The antigens contemplated for use in this invention include any antigen against which it is desired to elicit an immune response, and in particular, include any antigen for which a therapeutic immune response against such antigen would be beneficial to an individual. For example, the antigens can include, but are not limited to, any antigens associated with a pathogen, including viral antigens, fungal antigens, bacterial antigens, helminth antigens, parasitic antigens, ectoparasite antigens, protozoan antigens, or antigens from any other infectious agent. Antigens can also include any antigens associated with a particular disease or condition, whether from pathogenic or cellular sources, including, but not limited to, cancer antigens, antigens associated with an autoimmune disease (e.g., diabetes antigens), allergy antigens (allergens), mammalian cell molecules harboring one or more mutated amino acids, proteins normally expressed pre- or neo-natally by mammalian cells, proteins whose expression is induced by insertion of an epidemiologic agent (e.g. virus), proteins whose expression is induced by gene translocation, and proteins whose expression is induced by mutation of regulatory sequences. These antigens can be native antigens or genetically engineered antigens which have been modified in some manner (e.g., sequence change or generation of a fusion protein). It will be appreciated that in some embodiments (i.e., when the antigen is expressed by the yeast vehicle from a recombinant nucleic acid molecule), the antigen can be a protein or any epitope or immunogenic domain thereof, a fusion protein, or a chimeric protein, rather than an entire cell or microorganism.

Other antigens that are useful in yeast-based immunotherapy compositions of the present invention include antigens that may be relevant to suppressing an undesired, or harmful, immune response, such as is caused, for example, by allergens, autoimmune antigens, inflammatory agents, antigens involved in GVHD, certain cancers, septic shock antigens, and antigens involved in transplantation rejection.

In one aspect of the invention, antigens useful in one or more immunotherapy compositions of the invention include any cancer or tumor-associated antigen. In one aspect, the antigen includes an antigen associated with a preneoplastic or hyperplastic state. The antigen may also be associated with, or causative of cancer. Such an antigen may be tumor-specific antigen, tumor-associated antigen (TAA) or tissue-specific antigen, epitope thereof, and epitope agonist thereof. Cancer antigens include, but are not limited to, antigens from any tumor or cancer, including, but not limited to, melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, leukemias, lymphomas, primary hepatic cancers, lung cancers, pancreatic cancers, gastrointestinal cancers (including colorectal cancers), renal cell carcinomas, hematopoietic neoplasias and metastatic cancers thereof.

Suitable cancer antigens include but are not limited to carcinoembryonic antigen (CEA) and epitopes thereof such as CAP-1, CAP-1-6D (GenBank Accession No. M29540), MART-1 (Kawakami et al, J. Exp. Med. 180:347-352, 1994), MAGE-1 (U.S. Pat. No. 5,750,395), MAGE-3, GAGE (U.S. Pat. No. 5,648,226), GP-100 (Kawakami et al Proc. Nat'l Acad. Sci. USA 91:6458-6462, 1992), MUC-1, MUC-2, point mutated Ras oncoprotein, normal and point mutated p53 oncoproteins (Hollstein et al Nucleic Acids Res. 22:3551-3555, 1994), PSMA (Israeli et al Cancer Res. 53:227-230, 1993), tyrosinase (Kwon et al PNAS 84:7473-7477, 1987), TRP-1 (gp75) (Cohen et al Nucleic Acid Res. 18:2807-2808, 1990; U.S. Pat. No. 5,840,839), NY-ESO-1 (Chen et al PAS 94: 1914-1918, 1997), TRP-2 (Jackson et al EMBOJ, 11:527-535, 1992), TAG72, KSA, CA-125, PSA, HER-2/neu/c-erb/B2, (U.S. Pat. No. 5,550,214), EGFR, hTERT, p73, B-RAF, adenomatous polyposis coli (APC), Myc, von Hippel-Lindau protein (VHL), Rb-1, Rb-2, androgen receptor (AR), Smad4, MDR1, Flt-3, BRCA-1, BRCA-2, Bcr-Abl, pax3-fkhr, ews-fli-1, Brachyury, HERV-H, HERV-K, TWIST, Mesothelin, NGEP, modifications of such antigens and tissue specific antigens, splice variants of such antigens, and/or epitope agonists of such antigens. Other cancer antigens are known in the art. Other cancer antigens may also be identified, isolated and cloned by methods known in the art such as those disclosed in U.S. Pat. No. 4,514,506. Cancer antigens may also include one or more growth factors and splice variants of each.

Cancer antigens can also be non-self neoantigens created by genetic mutations in normal cellular proteins within tumors. These new mutations can create novel T cell neoepitiopes and as such represent a vast array of potential new targets for yeast-based immunotherapy.

In one aspect of the invention, antigens useful in one or more immunotherapy compositions of the invention include any antigens associated with a pathogen or a disease or condition caused by or associated with a pathogen. Such antigens include, but are not limited to, any antigens associated with a pathogen, including viral antigens, fungal antigens, bacterial antigens, helminth antigens, parasitic antigens, ectoparasite antigens, protozoan antigens, or antigens from any other infectious agent.

In one aspect, the antigen is from virus, including, but not limited to, adenoviruses, arena viruses, bunyaviruses, coronaviruses, coxsackie viruses, cytomegaloviruses, Epstein-Barr viruses, flaviviruses, hepadnaviruses, hepatitis viruses, herpes viruses, influenza viruses, lentiviruses, measles viruses, mumps viruses, myxoviruses, orthomyxoviruses, papilloma viruses, papovaviruses, parainfluenza viruses, paramyxoviruses, parvoviruses, picornaviruses, pox viruses, rabies viruses, respiratory syncytial viruses, reoviruses, rhabdoviruses, rubella viruses, togaviruses, and varicella viruses. Other viruses include T-lymphotrophic viruses, such as human T-cell lymphotrophic viruses (HTLVs, such as HTLV-I and HTLV-II), bovine leukemia viruses (BLVS) and feline leukemia viruses (FLVs). The lentiviruses include, but are not limited to, human (HIV, including HIV-1 or HIV-2), simian (SIV), feline (FIV) and canine (CIV) immunodeficiency viruses. In one embodiment, viral antigens include those from non-oncogenic viruses.

In another aspect, the antigen is from an infectious agent from a genus selected from: *Aspergillus, Bordatella, Brugia, Candida, Chlamydia, Coccidia, Cryptococcus, Dirofilaria, Escherichia, Francisella, Gonococcus, Histoplasma, Leishmania, Mycobacterium, Mycoplasma, Paramecium, Pertussis, Plasmodium, Pneumococcus, Pneumocystis, Rickettsia, Salmonella, Shigella, Staphylococcus, Streptococcus, Toxoplasma, Vibriocholerae,* and *Yersinia*. In one aspect, the infectious agent is selected from *Plasmodium falciparum* or *Plasmodium vivax*.

In one aspect, the antigen is from a bacterium from a family selected from: Enterobacteriaceae, Micrococcaceae, Vibrionaceae, Pasteurellaceae, Mycoplasmataceae, and Rickettsiaceae. In one aspect, the bacterium is of a genus selected from: *Pseudomonas, Bordetella, Mycobacterium, Vibrio, Bacillus, Salmonella, Francisella, Staphylococcus, Streptococcus, Escherichia, Enterococcus, Pasteurella*, and *Yersinia*. In one aspect, the bacterium is from a species selected from: *Pseudomonas aeruginosa, Pseudomonas mallei, Pseudomonas pseudomallei, Bordetella pertussis, Mycobacterium tuberculosis, Mycobacterium leprae, Francisella tularensis, Vibrio cholerae, Bacillus anthracis, Salmonella enteric, Yersinia pestis, Escherichia coli* and *Bordetella bronchiseptica*.

In one aspect, the antigen is from a fungus, such a fungus including, but not limited to, a fungus from *Saccharomyces* spp., *Aspergillus* spp., *Cryptococcus* spp., *Coccidioides* spp., *Neurospora* spp., *Histoplasma* spp., or *Blastomyces* spp. In one aspect, the fungus is from a species selected from: *Aspergillus fumigatus, A. flavus, A. niger, A. terreus, A. nidulans, Coccidioides immitis, Coccidioides posadasii* or *Cryptococcus neoformans*. The most common species of *Aspergillus* causing invasive disease include *A. fumigatus, A. flavus, A. niger, A. terreus* and *A. nidulans*, and may be found, for example, in patients who have immunosuppression or T-cell or phagocytic impairment. *A. fumigatus* has been implicated in asthma, aspergillomas and invasive aspergillosis. Coccidioidomycosis, also known as San Joaquin Valley Fever, is a fungal disease caused by *Coccidioides immitis*, and can lead to acute respiratory infections and chronic pulmonary conditions or dissemination to the meninges, bones, and joints. Cryptococcosis-associated conditions are also targeted by methods of the invention, for example, in a non-immunosuppressed or immunosuppressed subject, such as a subject who is infected with HIV.

In some embodiments, the antigen is a fusion protein. In one aspect of the invention, fusion protein can include two or more antigens. In one aspect, the fusion protein can include two or more immunogenic domains or two or more epitopes of one or more antigens. An immunotherapeutic composition containing such antigens may provide antigen-specific immunization in a broad range of patients. For example, a multiple domain fusion protein useful in the present invention may have multiple domains, wherein each domain consists of a peptide from a particular protein, the peptide consisting of at least 4 amino acid residues flanking either side of and including a mutated amino acid that is found in the protein, wherein the mutation is associated with a particular disease or condition.

In one embodiment, fusion proteins that are used as a component of the yeast-based immunotherapeutic composition useful in the invention are produced using constructs that are particularly useful for the expression of heterologous antigens in yeast. Typically, the desired antigenic protein(s) or peptide(s) are fused at their amino-terminal end to: (a) a specific synthetic peptide that stabilizes the expression of the fusion protein in the yeast vehicle or prevents posttranslational modification of the expressed fusion protein (such peptides are described in detail, for example, in U.S. Patent Publication No. 2004-0156858 A1, published Aug. 12, 2004, incorporated herein by reference in its entirety); (b) at least a portion of an endogenous yeast protein, wherein either fusion partner provides significantly enhanced stability of expression of the protein in the yeast and/or a prevents post-translational modification of the proteins by the yeast cells (such proteins are also described in detail, for example, in U.S. Patent Publication No. 2004-0156858 A1, supra); and/or (c) at least a portion of a yeast protein that causes the fusion protein to be expressed on the surface of the yeast (e.g., an Aga protein, described in more detail herein). In addition, the present invention includes the use of peptides that are fused to the C-terminus of the antigen-encoding construct, particularly for use in the selection and identification of the protein. Such peptides include, but are not limited to, any synthetic or natural peptide, such as a peptide tag (e.g., 6×His) or any other short epitope tag. Peptides attached to the C-terminus of an antigen according to the invention can be used with or without the addition of the N-terminal peptides discussed above.

In one embodiment, a synthetic peptide useful in a fusion protein is linked to the N-terminus of the antigen, the peptide consisting of at least two amino acid residues that are heterologous to the antigen, wherein the peptide stabilizes the expression of the fusion protein in the yeast vehicle or prevents posttranslational modification of the expressed fusion protein. The synthetic peptide and N-terminal portion of the antigen together form a fusion protein that has the following requirements: (1) the amino acid residue at position one of the fusion protein is a methionine (i.e., the first amino acid in the synthetic peptide is a methionine); (2) the amino acid residue at position two of the fusion protein is not a glycine or a proline (i.e., the second amino acid in the synthetic peptide is not a glycine or a proline); (3) none of the amino acid residues at positions 2-6 of the fusion protein is a methionine (i.e., the amino acids at positions 2-6, whether part of the synthetic peptide or the protein, if the synthetic peptide is shorter than 6 amino acids, do not include a methionine); and (4) none of the amino acids at positions 2-6 of the fusion protein is a lysine or an arginine (i.e., the amino acids at positions 2-6, whether part of the synthetic peptide or the protein, if the synthetic peptide is shorter than 5 amino acids, do not include a lysine or an arginine). The synthetic peptide can be as short as two amino acids, but in one aspect, is at least 2-6 amino acids (including 3, 4, 5 amino acids), and can be longer than 6 amino acids, in whole integers, up to about 200 amino acids, 300 amino acids, 400 amino acids, 500 amino acids, or more.

In one embodiment, a fusion protein comprises an amino acid sequence of M-X2-X3-X4-X5-X6, wherein M is methionine; wherein X2 is any amino acid except glycine, proline, lysine or arginine; wherein X3 is any amino acid except methionine, lysine or arginine; wherein X4 is any amino acid except methionine, lysine or arginine; wherein X5 is any amino acid except methionine, lysine or arginine; and wherein X6 is any amino acid except methionine, lysine or arginine. In one embodiment, the X6 residue is a proline. An exemplary synthetic sequence that enhances the stability of expression of an antigen in a yeast cell and/or prevents post-translational modification of the protein in the yeast includes the sequence M-A-D-E-A-P (SEQ ID NO:10). In addition to the enhanced stability of the expression product, this fusion partner does not appear to negatively impact the immune response against the vaccinating antigen in the construct. In addition, the synthetic fusion peptides can be designed to provide an epitope that can be recognized by a selection agent, such as an antibody.

The present invention includes the delivery (administration, immunization) of a composition of the invention to a subject. The administration process can be performed ex vivo or in vivo, but is typically performed in vivo. Ex vivo administration refers to performing part of the delivery step outside of the patient, such as administering a composition of the present invention to a population of cells (dendritic cells) removed from a patient under conditions such that a yeast vehicle, antigen(s) and any other agents or compositions are loaded into the cell, and returning the cells to the patient. This can include YL or YL mixed with tarmogen. The therapeutic composition of the present invention can be returned to a patient, or administered to a patient, by any suitable mode of administration.

Administration of a composition can be systemic, mucosal and/or proximal to the location of the target site (e.g., near a tumor). Suitable routes of administration will be apparent to those of skill in the art, depending on the type of condition to be prevented or treated, the antigen used, and/or the target cell population or tissue. Various acceptable methods of administration include, but are not limited to, intravenous administration, intraperitoneal administration, intramuscular administration, intranodal administration, intracoronary administration, intraarterial administration (e.g., into a carotid artery), subcutaneous administration, retroorbital administration, transdermal delivery, intratracheal administration, subcutaneous administration, intraarticular administration, intraventricular administration, inhalation (e.g., aerosol), intracranial, intraspinal, intraocular, aural, intranasal, oral, pulmonary administration, impregnation of a catheter, and direct injection into a tissue. In one aspect, routes of administration include: intravenous, intraperitoneal, subcutaneous, intradermal, intranodal, intramuscular, transdermal, inhaled, intranasal, oral, intraocular, intraarticular, intracranial, and intraspinal. Parenteral delivery can include intradermal, intramuscular, intraperitoneal, intrapleural, intrapulmonary, intravenous, subcutaneous, atrial catheter and venal catheter routes. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., Proc. Natl. Acad. Sci. USA 189:11277-11281, 1992, which is incorporated herein by reference in its entirety). Other routes of administration that modulate mucosal immunity are useful in the treatment of viral infections. Such routes include bronchial, intradermal, intramuscular, intranasal, other inhalatory, rectal, subcutaneous, topical, transdermal, vaginal and urethral routes. In one aspect, an immunotherapeutic composition of the invention is administered subcutaneously.

The immunogenic composition of the present invention can be formulated in a pharmaceutically acceptable excipient suitable for administration by injection of a subject.

With respect to the yeast-based immunotherapy compositions of the invention, in general, a suitable single dose is a dose that is capable of effectively providing a composition of the invention to a given cell type, tissue, or region of the patient body in an amount effective to elicit an antigen-specific immune response, when administered one or more times over a suitable time period. For example, in one embodiment, a single dose of a composition of the present invention is from about $1 \times 10^5$ to about $5 \times 10^7$ yeast cell equivalents per kilogram body weight of the organism being administered the composition. In one aspect, a single dose of a yeast vehicle of the present invention is from about 0.1 Y.U. ($1 \times 10^6$ cells) to about 200 Y.U. ($2 \times 10^9$ cells) per dose (i.e., per organism), including any interim dose, in increments of $0.1 \times 10^6$ cells (i.e., $1.1 \times 10^6$, $1.2 \times 10^6$, $1.3 \times 10^6$ . . . ). In one embodiment, doses include doses between 1 Y.U and 80 Y.U. and in one aspect, between 10 Y.U. and 40 Y.U. In one embodiment, the doses are administered at different sites on the individual but during the same dosing period. For example, a 40 Y.U. dose may be administered via by injecting 10 Y.U. doses to four different sites on the individual during one dosing period. In one embodiment, the dose of 1 Y.U to about 200 Y.U. includes both YL and Tarmogens.

"Boosters" or "boosts" of a therapeutic composition are administered, for example, when the immune response against the antigen has waned or as needed to provide an immune response or induce a memory response against a particular antigen or antigen(s). Boosters can be administered from about 1, 2, 3, 4, 5, 6, 7, or 8 weeks apart, to monthly, to bimonthly, to quarterly, to annually, to several years after the original administration. In one embodiment, an administration schedule is one in which from about $1 \times 10^5$ to about $5 \times 10^7$ yeast cell equivalents of a composition per kg body weight of the organism is administered at least 1, 2, 3, 4, 5, 6, 7, 8, 9, 10, or more times over a time period of from weeks, to months, to years.

The immunogenic composition of the present invention can be administered to the subject weekly, every other week and/or monthly. The composition can be administered once every 40 days. In still another aspect, the composition can be administered once every 60 days. In still another aspect, the composition can be administered once every 38 to 40 days.

In one aspect, inhalation of lysates for treatment of lung ailments. This could occur with or without mixture with intact Tarmogen and can be accomplished by pressurized metered dose inhalation (pMDIs), nebulizers, and dry powder inhalers (DPIs).

Methods of producing yeast vehicles and expressing, combining and/or associating yeast vehicles with antigens and/or other proteins and/or agents of interest to produce yeast-based immunotherapy compositions are contemplated by the invention.

According to the present invention, the term "yeast-lysate-antigen complex", "yeast vehicle-antigen complex" or "yeast-antigen complex" is used generically to describe any association of a yeast lysate or a yeast vehicle with an antigen, and can be used interchangeably with "yeast-based immunotherapy composition" when such composition is used to elicit an immune response as described above. Such association includes expression of the antigen by the yeast (a recombinant yeast), introduction of an antigen into a yeast, physical attachment of the antigen to the yeast, and mixing of the yeast and antigen together, such as in a buffer or other solution or formulation. These types of complexes are described in detail below. It will be recognized that yeast lysate-antigen complexes can be formed from yeast vehicle-antigen complexes by methods described herein.

In one embodiment, a yeast cell used to prepare the yeast vehicle is transfected with a heterologous nucleic acid molecule encoding a protein (e.g., the antigen or agent) such that the protein is expressed by the yeast cell. Such a yeast is also referred to herein as a recombinant yeast or a recombinant yeast vehicle. The yeast cell can then be loaded into the dendritic cell as an intact cell, or the yeast cell can be killed, or it can be derivatized such as by formation of yeast spheroplasts, cytoplasts, ghosts, or subcellular particles, any of which is followed by loading of the derivative into the dendritic cell. Yeast spheroplasts can also be directly transfected with a recombinant nucleic acid molecule (e.g., the spheroplast is produced from a whole yeast, and then transfected) in order to produce a recombinant spheroplast that expresses an antigen or other protein.

In one aspect, a yeast cell or yeast spheroplast used to prepare the yeast vehicle is transfected with a recombinant nucleic acid molecule encoding the antigen(s) or other protein such that the antigen or other protein is recombinantly expressed by the yeast cell or yeast spheroplast. In this aspect, the yeast cell or yeast spheroplast that recombinantly expresses the antigen(s) or other protein is used to produce a yeast vehicle comprising a yeast cytoplast, a yeast ghost, or a yeast membrane particle or yeast cell wall particle, or fraction thereof.

In general, the yeast vehicle and antigen(s) or other agent, can be associated by any technique described herein. In one aspect, the yeast vehicle was loaded intracellularly with the antigen(s) and/or agent(s). In another aspect, the antigen(s) and/or agent(s) was covalently or non-covalently attached to the yeast vehicle. In yet another aspect, the yeast vehicle and the antigen(s) and/or agent(s) were associated by mixing. In another aspect, and in one embodiment, the antigen(s) and/or agent(s) is expressed recombinantly by the yeast vehicle or by the yeast cell or yeast spheroplast from which the yeast vehicle was derived.

A number of antigens and/or other proteins to be produced by a yeast vehicle of the present invention is any number of antigens and/or other proteins that can be reasonably produced by a yeast vehicle, and typically ranges from at least one to at least about 6 or more, including from about 2 to about 6 heterologous antigens and or other proteins.

Expression of an antigen or other protein in a yeast vehicle of the present invention is accomplished using techniques known to those skilled in the art. Briefly, a nucleic acid molecule encoding at least one desired antigen or other protein is inserted into an expression vector in such a manner that the nucleic acid molecule is operatively linked to a transcription control sequence in order to be capable of effecting either constitutive or regulated expression of the nucleic acid molecule when transformed into a host yeast cell. Nucleic acid molecules encoding one or more antigens and/or other proteins can be on one or more expression vectors operatively linked to one or more expression control sequences. Particularly important expression control sequences are those which control transcription initiation, such as promoter and upstream activation sequences. Any suitable yeast promoter can be used in the present invention and a variety of such promoters are known to those skilled in the art. Promoters for expression in *Saccharomyces cerevisiae* include, but are not limited to, promoters of genes encoding the following yeast proteins: CUP1, alcohol dehydrogenase I (ADH1) or II (ADH2), phosphoglycerate kinase (PGK), triose phosphate isomerase (TPI), translational elongation factor EF-1 alpha (TEF2), glyceraldehyde-3-phosphate dehydrogenase (GAPDH; also referred to as TDH3, for triose phosphate dehydrogenase), galactokinase (GAL1), galactose-1-phosphate uridyl-transferase (GAL7), UDP-galactose epimerase (GAL10), cytochrome c1 (CYC1), Sec7 protein (SECT) and acid phosphatase (PH05), including hybrid promoters such as ADH2/GAPDH and CYC1/GAL10 promoters, and including the ADH2/GAPDH promoter, which is induced when glucose concentrations in the cell are low (e.g., about 0.1 to about 0.2 percent), as well as the CUP1 promoter and the TEF2 promoter. Likewise, a number of upstream activation sequences (UASs), also referred to as enhancers, are known. Upstream activation sequences for expression in *Saccharomyces cerevisiae* include, but are not limited to, the UASs of genes encoding the following proteins: PCK1, TPI, TDH3, CYC1, ADH1, ADH2, SUC2, GAL1, GAL7 and GAL10, as well as other UASs activated by the GAL4 gene product, with the ADH2 UAS being used in one aspect. Since the ADH2 UAS is activated by the ADR1 gene product, it may be preferable to overexpress the ADR1 gene when a heterologous gene is operatively linked to the ADH2 UAS. Transcription termination sequences for expression in *Saccharomyces cerevisiae* include the termination sequences of the α-factor, GAPDH, and CYC1 genes.

Transcription control sequences to express genes in methylotrophic yeast include the transcription control regions of the genes encoding alcohol oxidase and formate dehydrogenase.

Transfection of a nucleic acid molecule into a yeast cell according to the present invention can be accomplished by any method by which a nucleic acid molecule administered into the cell and includes, but is not limited to, diffusion, active transport, bath sonication, electroporation, microinjection, lipofection, adsorption, and protoplast fusion. Transfected nucleic acid molecules can be integrated into a yeast chromosome or maintained on extrachromosomal vectors using techniques known to those skilled in the art. Examples of yeast vehicles carrying such nucleic acid molecules are disclosed in detail herein. As discussed above, yeast cytoplast, yeast ghost, and yeast membrane particles or cell wall preparations can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplast, ghost or subcellular yeast membrane extract or fractions thereof containing desired antigens or other proteins.

Effective conditions for the production of recombinant yeast vehicles and expression of the antigen and/or other protein (e.g., an agent as described herein) by the yeast vehicle include an effective medium in which a yeast strain can be cultured. An effective medium is typically an aqueous medium comprising assimilable carbohydrate, nitrogen and phosphate sources, as well as appropriate salts, minerals, metals and other nutrients, such as vitamins and growth factors. The medium may comprise complex nutrients or may be a defined minimal medium. Yeast strains of the present invention can be cultured in a variety of containers, including, but not limited to, bioreactors, Erlenmeyer flasks, test tubes, microtiter dishes, and Petri plates. Culturing is carried out at a temperature, pH and oxygen content appropriate for the yeast strain. Such culturing conditions are well within the expertise of one of ordinary skill in the art (see, for example, Guthrie et al. (eds.), 1991, Methods in Enzymology, vol. 194, Academic Press, San Diego).

In some aspects of the invention, the yeast are grown under neutral pH conditions, and particularly, in a media maintained at a pH level of at least 5.5, namely the pH of the culture media is not allowed to drop below pH 5.5. In other aspects, the yeast is grown at a pH level maintained at about 5.5. In other aspects, the yeast is grown at a pH level maintained at about 5.6, 5.7, 5.8 or 5.9. In another aspect, the yeast is grown at a pH level maintained at about 6. In another aspect, the yeast is grown at a pH level maintained at about 6.5. In other aspects, the yeast is grown at a pH level maintained at about 6, 6.1, 6.2, 6.3, 6.4, 6.5, 6.6, 6.7, 6.8, 6.9 or 7.0. In other aspects, the yeast is grown at a pH level maintained at about 7, 7.1, 7.2, 7.3, 7.4, 7.5, 7.6, 7.7, 7.8, 7.9, or 8.0. The pH level is important in the culturing of yeast. One of skill in the art will appreciate that the culturing process includes not only the start of the yeast culture but the maintenance of the culture as well. As yeast culturing is known to turn acidic (i.e., lowering the pH) over time, care must be taken to monitor the pH level during the culturing process. Yeast cell cultures whereby the pH level of the medium drops below 6 are still contemplated within the scope of the invention provided that the pH of the media is brought up to at least 5.5 at some point during the culturing process. As such, the longer time the yeast are grown in a medium that is at least pH 5.5 or above, the better the results will be in terms of obtaining yeast with desirable characteristics.

In one aspect, yeast is cultured such that the pH level of the medium does not drop below pH 5.5. In some cases, the drop below pH 5.5 is not more than 5 minutes. In other cases, the drop below pH 5.5 is not more than 10 minutes. In other cases, the drop below pH 5.5 is not more than 1 hour. In another aspect, yeast is cultured such that the pH level of the medium does not drop below 5.0. In some cases, the drop below pH 5.0 is not more than 5 minutes. In other cases, the drop below pH 5.0 is not more than 10 minutes, preferably 20, 30, 40, 50 or 60 minutes. In other cases, the drop below pH 5.0 is not more than 1 hour. As such, the longer time the yeast are grown in a medium that is at least pH 5.5 or above, the better the results will be in terms of obtaining yeast with desirable characteristics described infra.

In one aspect, the use of neutral pH methods to grow yeast cells means that the yeast cells are grown in neutral pH for at least 50% of the time that the yeast are in culture. It is more preferable that the yeast are grown at neutral pH for at least 60% of the time they are in culture, more preferably at least 70% of the time they are in culture, more preferably at least 80% of the time they are in culture, and most preferably at least 90% of the time they are in culture.

In another aspect, growing yeast at neutral pH includes culturing yeast cells for at least five minutes at neutral pH, preferably at least 15 minutes at neutral pH, more preferably at least one hour at neutral pH, more preferably at least two hours, even more preferably, at least three hours or longer.

As used herein, the general use of the term "neutral pH" refers to a pH range between about pH 5.5 and about pH 8, and in one aspect, between about pH 6 and about 8. One of skill the art will appreciate that minor fluctuations (e.g., tenths or hundredths) can occur when measuring with a pH meter. As such, the use of neutral pH to grow yeast cells means that the yeast cells are grown in neutral pH for the majority of the time that they are in culture. The use of a neutral pH in culturing yeast promotes several biological effects that are desirable characteristics for using the yeast as vehicles for immunomodulation. In one aspect, culturing the yeast in neutral pH allows for good growth of the yeast without any negative effect on the cell generation time (e.g., slowing down the doubling time). The yeast can continue to grow to high densities without losing their cell wall pliability. In another aspect, the use of a neutral pH allows for the production of yeast with pliable cell walls and/or yeast that are sensitive to cell wall digesting enzymes (e.g., glucanase) at all harvest densities. This trait is desirable because yeast with flexible cell walls can induce unusual immune responses, such as by promoting the secretion of cytokines (e.g., interferon-γ (IFN-γ)) in the cells hosting the yeast. In addition, greater accessibility to the antigens located in the cell wall is afforded by such culture methods. In another aspect, the use of neutral pH for some antigens allows for release of the di-sulfide bonded antigen by treatment with dithiothreitol (DTT) that is not possible when such an antigen-expressing yeast is cultured in media at lower pH (e.g., pH 5). Finally, in another aspect, yeast cultured using the neutral pH methodologies, elicit increased production of at least TH1-type cytokines including, but not limited to, IFN-γ, interleukin-12 (IL-12), and IL-2, and may also elicit increased production of other cytokines, such as proinflammatory cytokines (e.g., IL-6).

In one embodiment, control of the amount of yeast glycosylation is used to control the expression of antigens by the yeast, particularly on the surface. The amount of yeast glycosylation can affect the immunogenicity and antigenicity of the antigen expressed on the surface, since sugar moieties tend to be bulky. As such, the existence of sugar moieties on the surface of yeast and its impact on the three-dimensional space around the target antigen(s) should be considered in the modulation of yeast according to the invention. Any method can be used to reduce the amount of glycosylation of the yeast (or increase it, if desired). For example, one could use a yeast mutant strain that has been selected to have low glycosylation (e.g. mnn1, och1 and mnn9 mutants), or one could eliminate by mutation the glycosylation acceptor sequences on the target antigen. Alternatively, one could use a yeast with abbreviated glycosylation patterns, e.g. *Pichia*. One can also treat the yeast using methods that reduce or alter the glycosylation.

In one embodiment of the present invention, as an alternative to expression of an antigen or other protein recombinantly in the yeast vehicle, a yeast vehicle is loaded intracellularly with the protein or peptide, or with carbohydrates or other molecules that serve as an antigen and/or are useful as immunomodulatory agents or biological response modifiers according to the invention. Subsequently, the yeast vehicle, which now contains the antigen and/or other proteins intracellularly, can be administered to the patient or loaded into a carrier such as a dendritic cell. Peptides and proteins can be inserted directly into yeast vehicles of the present invention by techniques known to those skilled in the art, such as by diffusion, active transport, liposome fusion, electroporation, phagocytosis, freeze-thaw cycles and bath sonication. Yeast vehicles that can be directly loaded with peptides, proteins, carbohydrates, or other molecules include intact yeast, as well as spheroplasts, ghosts or cytoplasts, which can be loaded with antigens and other agents after production. Alternatively, intact yeast can be loaded with the antigen and/or agent, and then spheroplasts, ghosts, cytoplasts, or subcellular particles can be prepared therefrom. Any number of antigens and/or other agents can be loaded into a yeast vehicle in this embodiment, from at least 1, 2, 3, 4 or any whole integer up to hundreds or thousands of antigens and/or other agents, such as would be provided by the loading of a microorganism, by the loading of a mammalian tumor cell, or portions thereof, for example.

In another embodiment of the present invention, an antigen and/or other agent is physically attached to the yeast vehicle. Physical attachment of the antigen and/or other agent to the yeast vehicle can be accomplished by any method suitable in the art, including covalent and non-covalent association methods which include, but are not limited to, chemically crosslinking the antigen and/or other agent to the outer surface of the yeast vehicle or biologically linking the antigen and/or other agent to the outer surface of the yeast vehicle, such as by using an antibody or other binding partner. Chemical cross-linking can be achieved, for example, by methods including glutaraldehyde linkage, photoaffinity labeling, treatment with carbodiimides, treatment with chemicals capable of linking di-sulfide bonds, and treatment with other cross-linking chemicals standard in the art. Alternatively, a chemical can be contacted with the yeast vehicle that alters the charge of the lipid bilayer of yeast membrane or the composition of the cell wall so that the outer surface of the yeast is more likely to fuse or bind to antigens and/or other agent having particular charge characteristics. Targeting agents such as antibodies, binding peptides, soluble receptors, and other ligands may also be incorporated into an antigen as a fusion protein or otherwise associated with an antigen for binding of the antigen to the yeast vehicle.

When the antigen or other protein is expressed on or physically attached to the surface of the yeast, spacer arms may, in one aspect, be carefully selected to optimize antigen or other protein expression or content on the surface. The size of the spacer arm(s) can affect how much of the antigen or other protein is exposed for binding on the surface of the yeast. Thus, depending on which antigen(s) or other protein(s) are being used, one of skill in the art will select a spacer arm that effectuates appropriate spacing for the antigen or other protein on the yeast surface. In one embodiment, the spacer arm is a yeast protein of at least 450 amino acids. Spacer arms have been discussed in detail above.

Another consideration for optimizing antigen surface expression is whether the antigen and spacer arm combination should be expressed as a monomer or as dimer or as a trimer, or even more units connected together. This use of monomers, dimers, trimers, etc. allows for appropriate spacing or folding of the antigen such that some part, if not all, of the antigen is displayed on the surface of the yeast vehicle in a manner that makes it more immunogenic.

In yet another embodiment, the yeast vehicle and the antigen or other protein are associated with each other by a more passive, non-specific or non-covalent binding mechanism, such as by gently mixing the yeast vehicle and the antigen or other protein together in a buffer or other suitable formulation (e.g., admixture).

In one embodiment of the invention, the yeast vehicle and the antigen or other protein are both loaded intracellularly into a carrier such as a dendritic cell or macrophage to form the therapeutic composition or vaccine of the present invention. Alternatively, an antigen or other protein can be loaded into a dendritic cell in the absence of the yeast vehicle.

In one embodiment of the invention, yeast vehicles useful in the invention include yeast vehicles that have been killed or inactivated. Killing or inactivating of yeast can be accomplished by any of a variety of suitable methods known in the art. For example, heat inactivation of yeast is a standard way of inactivating yeast, and one of skill in the art can monitor the structural changes of the target antigen, if desired, by standard methods known in the art. Making yeast lysates as described herein in another way of inactivating the yeast. Alternatively, other methods of inactivating the yeast can be used, such as chemical, electrical, radioactive or UV methods. See, for example, the methodology disclosed in standard yeast culturing textbooks such as Methods of Enzymology, Vol. 194, Cold Spring Harbor Publishing (1990). Any of the inactivation strategies used should take the secondary, tertiary or quaternary structure of the target antigen into consideration and preserve such structure as to optimize its immunogenicity.

Yeast lysate and yeast vehicles can be formulated into yeast-based immunotherapy compositions or products of the present invention, including preparations to be administered to a subject directly or first loaded into a carrier such as a dendritic cell, using a number of techniques known to those skilled in the art. For example, yeast vehicles can be dried by lyophilization. Formulations comprising yeast vehicles can also be prepared by packing yeast in a cake or a tablet, such as is done for yeast used in baking or brewing operations. In one aspect, the yeast lysates and yeast vehicles can be frozen. In addition, yeast vehicles can be mixed with a pharmaceutically acceptable excipient, such as an isotonic buffer that is tolerated by a host or host cell. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity-enhancing agents, such as sodium carboxymethylcellulose, sorbitol, glycerol or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise, for example, dextrose, human serum albumin, and/or preservatives to which sterile water or saline can be added prior to administration.

In one embodiment of the present invention, a composition can include biological response modifier compounds, or the ability to produce such modifiers (i.e., by transfection of the yeast vehicle with nucleic acid molecules encoding such modifiers. Biological response modifiers have been described above.

Compositions of the invention can further include any other compounds that are useful for protecting a subject from a particular disease or condition, including an infectious disease or cancer, or any compounds that treat or ameliorate any symptom of such an infection.

The invention also includes a kit comprising any of the compositions described herein, or any of the individual components of the compositions described herein. Reagents may be present in free form or immobilized to a substrate such as a plastic dish, microarray plate, a test tube, a test rod and so on. The kit can also include suitable reagents for the detection of the reagent and/or for the labeling of positive or negative controls, wash solutions, dilution buffers and the like. The kit can also include a set of written instructions for using the kit and interpreting the results. In one embodiment, the kit is formulated to be a high-throughput assay. Kits may be prepared and used for any clinical, research or diagnostic method of the invention.

With respect to agents useful in the invention, a protein or antibody is administered, in one aspect, in an amount that is between about 50 U/kg and about 15,000 U/kg body weight of the subject. In another embodiment, a protein or antibody is administered in an amount that is between about 0.01 µg and about 10 mg per kg body weight of the patient, and more preferably, between about 0.1 µg and about 100 µg per kg body weight of the patient. When the compound to be delivered is a nucleic acid molecule, an appropriate single dose results in at least about 1 µg of protein expressed per mg of total tissue protein per µg of nucleic acid delivered. Small molecules are delivered according to the preferred dosage specified for the given small molecule and can be determined by those of skill in the art.

In one aspect of the invention, an agent is administered concurrently with the yeast-based immunotherapy composition. In one aspect of the invention, an agent is administered sequentially with the yeast-based immunotherapy composition. In another embodiment, an agent is administered before the yeast-based immunotherapy composition is administered. In another embodiment, an agent is administered after the yeast-based immunotherapy composition is administered. In one embodiment, an agent is administered in alternating doses with the yeast-based immunotherapy composition, or in a protocol in which the yeast-based composition is administered at prescribed intervals in between or with one or more consecutive doses of an agent, or vice versa. In one embodiment, the yeast-based immunotherapy composition is administered in one or more doses over a period of time prior to commencing the administration of an agent. In other words, the yeast-based immunotherapeutic composition is administered as a monotherapy for a period of time, and then the agent administration is added, either concurrently with new doses of yeast-based immunotherapy, or in an alternating fashion with yeast-based immunotherapy. Alternatively, an agent may be administered for a period of time prior to beginning administration of the yeast-based immunotherapy composition. In one aspect, the yeast is engineered to express or carry an agent, or a different yeast is engineered or produced to express or carry an agent.

A virus-based immunotherapy composition typically comprises a viral vector comprising a virus genome or portions thereof (e.g., a recombinant virus) and a nucleic acid sequence encoding at least one antigen(s) from a disease-causing agent or disease state (e.g., a cancer antigen(s), infectious disease antigen(s), and/or at least one immunogenic domain thereof). In some embodiments, a virus-based immunotherapy composition further includes at least one viral vector comprising one or more nucleic acid sequences encoding one or more immunostimulatory molecule(s). In some embodiments, the genes encoding immunostimulatory molecules and antigens are inserted into the same viral vector (the same recombinant virus).

As used herein with respect to administration of a composition, the term "concurrently" means to administer each of the compositions and particularly, the first dose of such compositions, essentially at the same time or within the same dosing period, or within a time period during which the initial effects of priming of the immune system by the immunotherapy composition occurs (e.g., within 1-2 days or less). For clarity, concurrent administration does not require administration of all of the compositions at precisely the same moment, but rather, the administration of all compositions should occur within one scheduled dosing of the patient in order to prime the immune system and achieve the effect of the agent concurrently (e.g., one composition may be administered first, followed immediately or closely by the administration of the second composition, and so on). In some circumstances, such as when the compositions are administered to the same site, the compositions may be provided in admixture, although even when administered at the same site, sequential administration of each composition during the same dosing period may be used. In one aspect, the compositions are administered within the same 1-2 days, and in another aspect on the same day, and in another aspect within the same 12 hour period, and in another aspect within the same 8 hour period, and in another aspect within the same 4 hour period, and in another aspect within the same 1, 2 or 3 hour period, and in another aspect, within the same 1, 2, 3, 4, 6, 7, 8, 9, or 10 minutes.

In one embodiment of the invention, the yeast-based immunotherapy composition and the agent(s) are administered concurrently, but to different physical sites in the patient. For example, one composition or agent can be administered to one or more sites of the individual's body and the other composition or agent can be administered to one or more different sites of the individual's body, e.g., on different sides of the body or near different draining lymph nodes. In another embodiment, the immunotherapy composition and the agent are administered concurrently and to the same or substantially adjacent sites in the patient. A substantially adjacent site is a site that is not precisely the same injection site to which the first composition or agent is administered, but that is in close proximity (is next to) the first injection site. In one embodiment, the immunotherapy composition and agent are administered in admixture. Some embodiments may include combinations of administration approaches.

In the method of the present invention, compositions and therapeutic compositions can be administered to animal, including any vertebrate, and particularly to any member of the Vertebrate class, Mammalia, including, without limitation, primates, rodents, livestock and domestic pets. Livestock include mammals to be consumed or that produce useful products (e.g., sheep for wool production). Mammals to protect include humans, dogs, cats, mice, rats, goats, sheep, cattle, horses and pigs.

An "individual" is a vertebrate, such as a mammal, including without limitation a human. Mammals include, but are not limited to, farm animals, sport animals, pets, primates, mice and rats. The term "individual" can be used interchangeably with the term "animal", "subject" or "patient".

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, Methods of Enzymology, Vol. 194, Guthrie et al., eds., Cold Spring Harbor Laboratory Press (1990); Biology and activities of yeasts, Skinner, et al., eds., Academic Press (1980); Methods in yeast genetics: a laboratory course manual, Rose et al., Cold Spring Harbor Laboratory Press (1990); The Yeast Saccharomyces: Cell Cycle and Cell Biology, Pringle et al., eds., Cold Spring Harbor Laboratory Press (1997); The Yeast Saccharomyces: Gene Expression, Jones et al., eds., Cold Spring Harbor Laboratory Press (1993); The Yeast Saccharomyces: Genome Dynamics, Protein Synthesis, and Energetics, Broach et al., eds., Cold Spring Harbor Laboratory Press (1992); Molecular Cloning: A Laboratory Manual, second edition (Sambrook et al., 1989) and Molecular Cloning: A Laboratory Manual, third edition (Sambrook and Russel, 2001), (jointly referred to herein as "Sambrook"); Current Protocols in Molecular Biology (F. M. Ausubel et al., eds., 1987, including supplements through 2001); PCR: The Polymerase Chain Reaction, (Mullis et al., eds., 1994); Harlow and Lane (1988) Antibodies, A Laboratory Manual, Cold Spring Harbor Publications, New York; Harlow and Lane (1999) Using Antibodies: A Laboratory Manual Cold Spring Harbor Laboratory Press, Cold Spring Harbor, NY (jointly referred to herein as "Harlow and Lane"), Beaucage et al. eds., Current Protocols in Nucleic Acid Chemistry John Wiley & Sons, Inc., New York, 2000); Casarett and Doull's Toxicology The Basic Science of Poisons, C. Klaassen, ed., 6th edition (2001), and Vaccines, S. Plotkin and W. Orenstein, eds., 3rd edition (1999).

General Definitions

A "TARMOGEN®" (GlobeImmune, Inc., Louisville, Colorado) generally refers to a yeast vehicle expressing one or more heterologous antigens extracellularly (on its surface), intracellularly (internally or cytosolically) or both extracellularly and intracellularly. TARMOGEN®s have been generally described (see, e.g., U.S. Pat. No. 5,830,463). Certain yeast-based immunotherapy compositions, and methods of making and generally using the same, are also described in detail, for example, in U.S. Pat. Nos. 5,830,463, 7,083,787, 7,736,642, Stubbs et al., *Nat. Med.* 7:625-629 (2001), Lu et al., *Cancer Research* 64:5084-5088 (2004), and in Bernstein et al., *Vaccine* 2008 Jan. 24; 26(4):509-21, each of which is incorporated herein by reference in its entirety.

As used herein, the term "analog" refers to a chemical compound that is structurally similar to another compound but differs slightly in composition (as in the replacement of one atom by an atom of a different element or in the presence of a particular functional group, or the replacement of one functional group by another functional group). Thus, an analog is a compound that is similar or comparable in function and appearance but has a different structure or origin with respect to the reference compound.

The terms "substituted", "substituted derivative" and "derivative", when used to describe a compound, means that at least one hydrogen bound to the unsubstituted compound is replaced with a different atom or a chemical moiety.

A "cell-mediated" immune response (which may be used interchangeably anywhere herein with the term "cellular" immune response) refers generally to the response to an antigen of immune cells including T lymphocytes (including cytotoxic T lymphocytes (CTL)), dendritic cells, macrophages, and natural killer cells, and to all of the processes that accompany such responses, including, but not limited to, activation and proliferation of these cells, CTL effector functions, cytokine production that influences the function of other cells involved in adaptive immune responses and innate immune responses, memory T cell generation, and stem cell-like memory cells.

"Vaccination" or "immunization" refers to the elicitation (induction) of an immune response against an antigen or immunogenic portion thereof, as a result of administration of the antigen, alone or together with an adjuvant. Vaccination results in a protective or therapeutic effect, wherein subsequent exposure to the antigen (or a source of the antigen) elicits an immune response against the antigen (or source) that reduces or prevents a disease or condition in the animal. The concept of vaccination is well known in the art. The immune response that is elicited by administration of an immunotherapeutic composition (vaccine) can be any detectable change in any facet of the immune response (e.g., cell-mediated response, humoral response, cytokine production), as compared to in the absence of the administration of the composition.

According to the present invention, "heterologous amino acids" are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Therefore, at least two amino acid residues that are heterologous to the antigen are any two amino acid residues that are not naturally found flanking the antigen.

According to the present invention, reference to a "heterologous" protein or "heterologous" antigen, including a heterologous fusion protein, in connection with a yeast vehicle of the invention means that the protein or antigen is not a protein or antigen that is naturally expressed by the yeast, although a fusion protein may include yeast sequences or proteins or portions thereof that are naturally expressed by yeast (e.g., an Aga protein as described herein). For example, a fusion protein of an influenza hemagglutinin protein and a yeast Aga protein is considered to be a heterologous protein with respect to the yeast vehicle for the purposes of the present invention, since such a fusion protein is not naturally expressed by a yeast.

According to the present invention, the phrase "selectively binds to" refers to the ability of an antibody, antigen-binding fragment or binding partner of the present invention to preferentially bind to specified proteins. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen-binding fragment thereof in the absence of the antigen is considered to be background. Binding can be measured using a variety of methods standard in the art including enzyme immunoassays (e.g., ELISA), immunoblot assays, etc.).

Reference to a protein or polypeptide in the present invention includes full-length proteins, fusion proteins, or any fragment, domain, conformational epitope, or homologue of such proteins. More specifically, an isolated protein, according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. In one aspect of the invention, an isolated protein of the present invention is produced recombinantly. According to the present invention, the terms "modification" and "mutation" can be used interchangeably, particularly with regard to modifications/mutations to the amino acid sequence of proteins or portions thereof.

As used herein, the term "homologue" is used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have either enhanced, decreased, or substantially similar properties as compared to the naturally occurring protein or peptide. A homologue can include an agonist of a protein or an antagonist of a protein. Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

A homologue of a given protein may comprise, consist essentially of, or consist of, an amino acid sequence that is at least about 45%, or at least about 50%, or at least about 55%, or at least about 60%, or at least about 65%, or at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein. In one embodiment, the homologue comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the naturally occurring amino acid sequence of the reference protein.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", FEMS Microbiol Lett. 174:247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

An isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene. An isolated nucleic acid molecule that includes a gene is not a fragment of a chromosome that includes such gene, but rather includes the coding region and regulatory regions associated with the gene, but no additional genes that are naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

A recombinant nucleic acid molecule is a molecule that can include at least one of any nucleic acid sequence encoding any one or more proteins described herein operatively linked to at least one of any transcription control sequence capable of effectively regulating expression of the nucleic acid molecule(s) in the cell to be transfected. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. In addition, the phrase "recombinant molecule" primarily refers to a nucleic acid molecule operatively linked to a transcription control sequence, but can be used interchangeably with the phrase "nucleic acid molecule" which is administered to an animal.

A recombinant nucleic acid molecule includes a recombinant vector, which is any nucleic acid sequence, typically a heterologous sequence, which is operatively linked to the isolated nucleic acid molecule encoding a fusion protein of the present invention, which is capable of enabling recombinant production of the fusion protein, and which is capable of delivering the nucleic acid molecule into a host cell according to the present invention. Such a vector can contain nucleic acid sequences that are not naturally found adjacent to the isolated nucleic acid molecules to be inserted into the vector. The vector can be either RNA or DNA, either prokaryotic or eukaryotic, and in one aspect of the present invention, is a virus or a plasmid. Recombinant vectors can be used in the cloning, sequencing, and/or otherwise manipulating of nucleic acid molecules, and can be used in delivery of such molecules (e.g., as in a DNA vaccine or a viral vector-based vaccine). Recombinant vectors may be used in the expression of nucleic acid molecules, and can also be referred to as expression vectors. Some recombinant vectors are capable of being expressed in a transfected host cell.

In a recombinant molecule of the present invention, nucleic acid molecules are operatively linked to expression vectors containing regulatory sequences such as transcription control sequences, translation control sequences, origins of replication, and other regulatory sequences that are compatible with the host cell and that control the expression of nucleic acid molecules of the present invention. In particular, recombinant molecules of the present invention include nucleic acid molecules that are operatively linked to one or more expression control sequences. The phrase "operatively linked" refers to linking a nucleic acid molecule to an expression control sequence in a manner such that the molecule is expressed when transfected (i.e., transformed, transduced or transfected) into a host cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as algae, bacteria and yeast. In microbial systems, the term "transformation" is used to describe an inherited change due to the acquisition of exogenous nucleic acids by the microorganism and is essentially synonymous with the term "transfection." Therefore, transfection techniques include, but are not limited to, transformation, chemical treatment of cells, particle bombardment, electroporation, microinjection, lipofection, adsorption, infection and protoplast fusion.

The following experimental results are provided for purposes of illustration and are not intended to limit the scope of the invention.

EXAMPLES

Example 1

The following example demonstrates that cleared lysates of TARMOGEN® mixed with intact TARMOGEN® elicit greater CTL killing activity than does intact TARMOGEN® alone. This result was shown for several different TARMOGEN® for which the heterologous antigen expressed in the yeast contained a SIINFEKL (SEQ ID NO:9) epitope of chicken ovalbumin.

Methods:
1. Lysates of each TARMOGEN® were prepared as follows: antigen expression was induced by copper addition (e.g. 375 μM for 3 h) from a copper-inducible promoter during the log phase of growth. The cells were washed, heat killed at 56° C. for 1 h. Heat killed Tarmogens were mixed with PBS and 500 μL of acid washed 0.2 μm glass beads in a 1.5 mL total volume and the mixture was vigorously shaken in a mechanical agitation machine ("Fast prep" or "Bead beater") until >97% of the cells were ruptured. The mixture was centrifuged for 5 minutes at 16,000 rpm, 25° C., and the lysate (supernatant), which is free of cell walls, membranes, and glass beads, was harvested.

2. Lysates were mixed with intact TARMOGEN® (2 YU each) plus 25 μg of anti-CD40 antibody, and the mixture was injected by the retro-orbital route to C57BL/6 mice.

Figure 2:
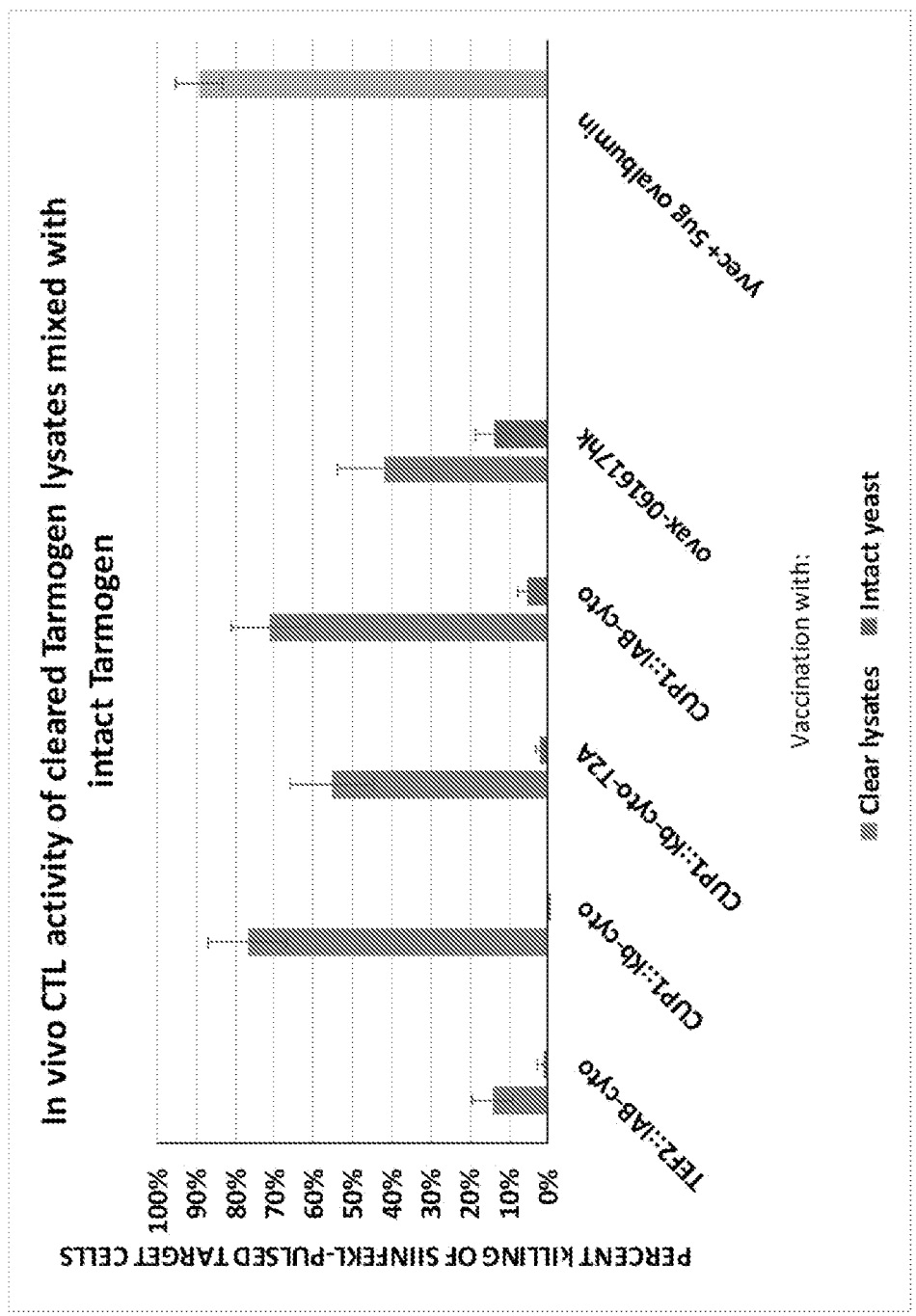
FIG. 2 shows that cleared lysates of Tarmogen (first bar in each set) mixed with intact Tarmogen (second bar in each set) are more effective than intact Tarmogen alone at generating CTL mediated killing in vivo. TEF2: a constitutive promoter of a yeast translation elongation factor; CUP1: the yeast copper-inducible promoter; Kb-cyto: Tarmogen (or lysate thereof) expressing a polyepitope with several B16F10 cell-derived, H-2Kb restricted neoepitopes plus a H-2Kb restricted SIINFEKL (SEQ ID NO:9) epitope; IAb-cyto: Tarmogen (or lysate thereof) expressing a polyepitope with several B16F10 cell-derived, IA(b)-binding neoepitopes plus the H-2Kb restricted SIINFEKL (SEQ ID NO:9) epitope; Yvec, empty yeast vector; Ovax; Tarmogen (or cleared yeast lysate (YL) thereof) expressing chicken ovalbumin.

3. 1 week later, the vaccinated mice were injected retroorbitally with naive syngeneic splenocytes that had been incubated "pulsed" with a 100 μg/mL solution of SIINFEKL (SEQ ID NO:9) peptide, washed to remove unbound peptide, and labeled with CFSE green dye for detection. An un-pulsed population that was labeled with a lower concentration of CFSE to distinguish it from the peptide-pulsed population was injected concurrently (internal control). FIG. 1 presents a diagram of this assay. The injected spleen cells home to the spleen. Peptide-pulsed cells will be killed if SIINFEKL (SEQ ID NO:9)-specific CTL had been generated by the vaccination. The extent of killing correlates with the vaccine efficacy.

4. Spleens were removed from the vaccinated, target cell-injected mice. The spleens were dispersed to single cell suspensions, red blood cells removed, and the extent of CTL-mediated killing measured by flow cytometry.

Example 2

This example demonstrates that cleared lysates of ovalbumin TARMOGEN® (ovax) mixed with intact Ovax generated near complete (95%) killing of SIINFEKL (SEQ ID NO:9)-pulsed targets, as compared to 0-20% killing observed in mice vaccinated with intact ovax. The experimental conditions were the same as in FIG. 1, except that injection of the vaccine was by tail vein instead of retroorbital (Table 1).

TABLE 1

In vivo CTL results in mice vaccinated with Tarmogen-lysates plus intact Tarmogen

| Vaccination with: | # mice | Avg % killing |
|---|---|---|
| Intact Ovax (2 YU) | 3 | 0-20% |
| Ovax (2 YU) + cleared lysate of ovax (2 YU) | 3 | 95% |
| Null | 3 | 0% |

Example 3

Figure 3:
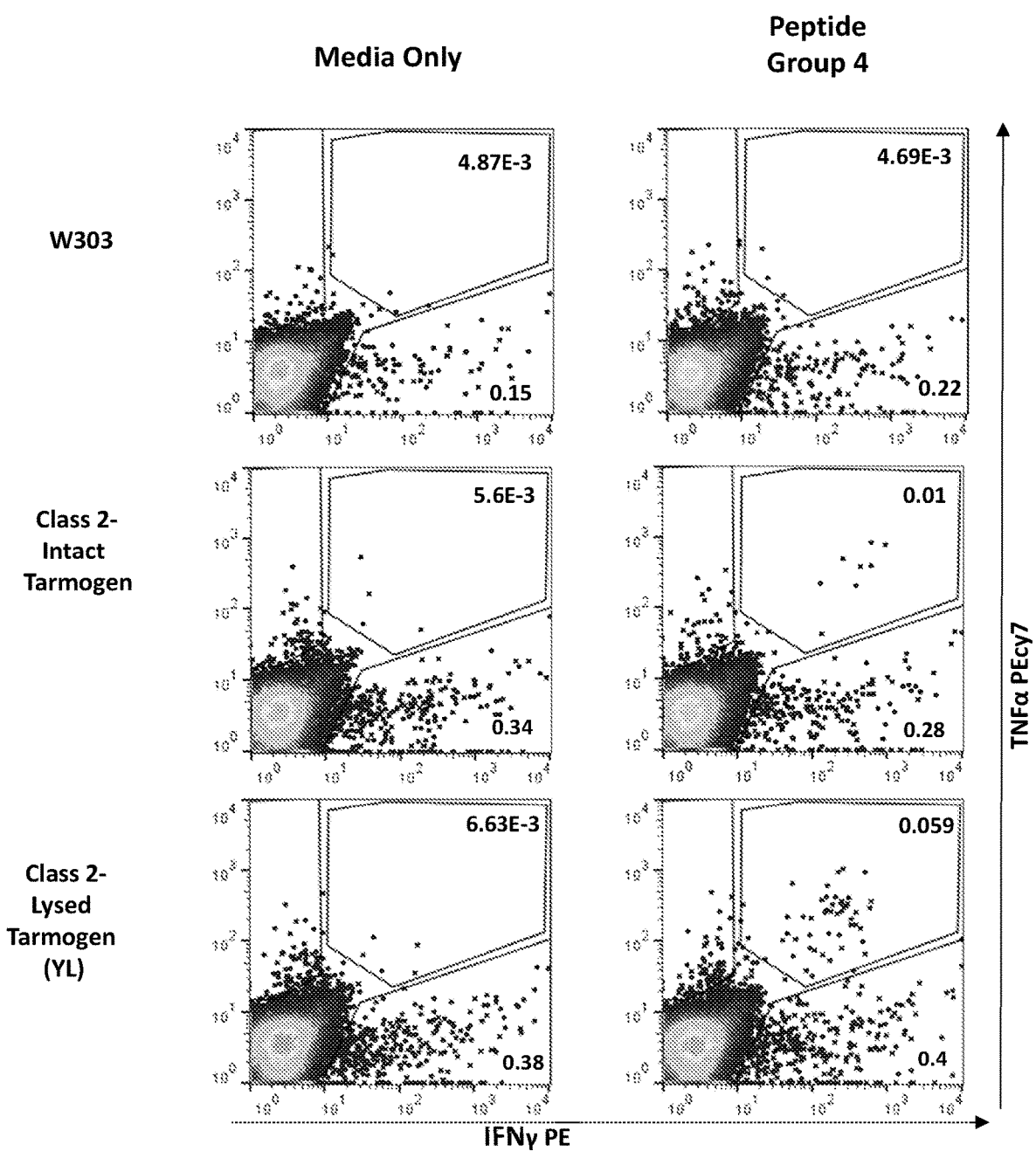
FIG. 3 shows ex-vivo intracellular cytokine staining of splenocytes from I-$A^b$-cyto Tarmogen immunized mice: intact vs. lysed Tarmogen. Two immunizations (homologous prime/boost) were conducted with W303 (empty control yeast), I-$A^b$-cyto intact yeast, or I-$A^b$-cyto cleared yeast lysate (YL). In vitro stimulants: media only, cRPMI+10% FBS; ESAT6, 5 µM of mTb ESAT6 peptide N-MTE-QQWNFAGIEAAASAIQG (SEQ ID NO:1); Peptide group 4, class II peptides Nant23 (qpysgspanVavytalvep) (SEQ ID NO:2), Nant24 (sgkhkyrqtAmftatmppa) (SEQ ID NO:3); Nant25 (nrtsvmfnfpEqatvkkvv) (SEQ ID NO:4), Nant26 (sfetashdgeagpsPevlq) (SEQ ID NO:5); Nant27 (mfnqgra-faAvrlpfcghk) (SEQ ID NO:6), Nant28 (lwvhslrrl-Lecfyvsvfs) (SEQ ID NO:7), and Nant29 (epmftfvypTifpl-retpm) (SEQ ID NO:8) where each uppercase residue within the peptide sequences is the B16F10 neo-mutation. Flow cytometry plots are shown for IFNγ and TNFα expression within CD3$^+$CD4$^+$ cells.

FIG. 3 shows ex-vivo intracellular cytokine staining of splenocytes from I-$A^b$-cyto Tarmogen immunized mice: intact vs. lysed Tarmogen. On day 0, mice were intradermally immunized with 2.5YU/flank (total of 5 YU/mouse) of W303a control yeast, I-$A^b$-cyto-Intact Tarmogen, or I-$A^b$ YL. On day 38, mice received a homologous booster vaccination, again with 2.5YU/flank (total of 5YU/mouse). Nine days after the booster vaccination (day 47), spleens were harvested and total splenocytes were stimulated with peptide pools (5 μM per peptide) or control peptides for 2 hours at 37° C. Brefeldin A was added and the cultures which were returned to 37° C. for an additional 4 hours, then stored overnight at 4° C. Cells were stained with fluorescent dye-labeled antibodies as described below ("Methods for FIG. 4"). Flow cytometry was performed using the Beckman Coulter CyAn instrument, with 1.5-2×$10^5$ $CD3^+$ cells collected per sample. Flow cytometry plots are shown for IFNγ and TNFα expression within $CD3^+CD4^+$ cells.

Example 4

This example shows YE-NEO-001-93 vaccination generates antigen-specific $CD4^+$ and $CD8^+$ cytokine production.

Immunization: Female C57BL/6 mice were immunized retro-orbitally with 2 YU of YE-NEO-001-93 YL+25 µg α-CD40 antibody+2 YU Yvec or with 2.5YU intact YE-NEO-001-93+25 µg α-CD40 antibody (n=2 mice per group). The injection volume was 150 µL for all mice. Due to smaller spleen size, three naïve, unimmunized mice that were gender- and age-matched were used as negative controls.

Splenocyte Harvest and In Vitro Stimulation: Spleens were harvested from naïve or vaccinated mice on day 7 post-immunization and all mice per condition were combined (n=3 naïve, n=2 for experimental vaccinations). Single cell suspensions were generated and red blood cells were lysed using ammonium chloride-potassium (ACK) lysis buffer. A total of 2×10$^6$ cells per well were stimulated with 5 µM of peptide (SIINFEKL) (SEQ ID NO:9), in a total volume of 200 uL in a 96 well U-bottom, tissue-culture treated plate. The DMSO negative stimulation controls contained the same amount of DMSO as the SIINFEKL (SEQ ID NO:9)—treated wells. Cells were incubated at 37° C., 5% CO2 for a total of 6 hours. BFA was added at time zero. After 6 hours, cells were stored at 4° C. for 12-18 hours.

Figure 4:
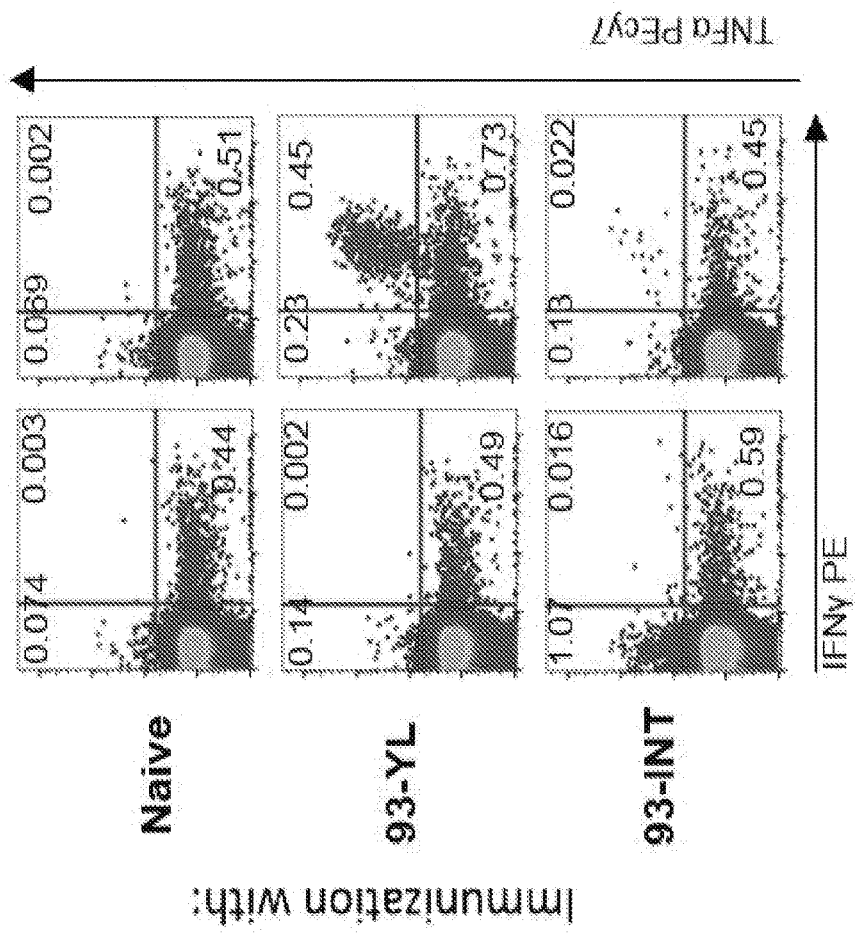
FIG. 4 shows YE-NEO-001-93 vaccination generates antigen-specific CD4$^+$ and CD8$^+$ cytokine production. Female C57BL/6 mice were immunized with: i) a mixture of 2 YU YL from the YE-NEO-001-93 prototype+2YU of empty-vector (Yvec) Tarmogen+25 µg α-CD40-antibody (93-YL), ii) 2.5 YU intact YE-NEO-001-93+25 µg αCD40 antibody (93-INT), or; iii) were left non-immunized as a negative control (Naïve). After 7 days, splenocytes were harvested and stimulated in vitro for 6 hours with peptides in the presence of Brefeldin A (BFA). Representative flow plots are shown in FIG. 4, showing the frequency of dual IFNγ$^+$TNFα$^+$-producing CD8$^+$ T cells generated following stimulation with SIINFEKL (SEQ ID NO:9) peptide or control (DMSO, medium with no peptide and containing solvent (DMSO) concentration matched to that used in peptide stimulations); SIINFEKL (SEQ ID NO:9), Ovalbumin peptide 257-264.

Intracellular Cytokine Staining and Flow Cytometry Analysis: The following day, ICS was performed using the eBioscience FoxP3/Transcription Factor Staining Buffer Set as follows. Cells were washed and then stained with CD8 ef450, CD4 APC-CY7, CD3 APC and FC block (24G2) a 1:200 in FACS buffer (PBS+2% FBS+2 mM EDTA) for 30 min on ice. Cells were then washed, and fixed/permeabilized. Intracellular staining was performed using IFNγ PE and TNFα PE-CY7 at 1:200 in FACS buffer in the presence of FC block and rat serum (2 uL/25 uL) for 30 min at RT. After washing, three wells per condition were combined into a single sample in FACS buffer and analyzed using the BD FACSVerse™ Flow Cytometer. A total of two replicates were analyzed per condition, with 2-3×10$^5$ CD3$^+$ cells collected per replicate for analysis. Data was analyzed using FlowJo v10. As can be seen in FIG. 4, the lysates produce antigen specific signals that are 20-fold stronger than intact yeast.

Example 5

The example shows that Tarmogen cleared lysate enhances anti-tumor activity over intact Tarmogen alone.

Mice were vaccinated with intact Tarmogen alone or Tarmogen plus YL (once per week for a total of 3 injections, subcutaneously (sc), both flanks). One week after the 3rd immunization, mice were challenged sc with 30,000 B16F10 cells in the right flank, posterior to immunization site. These B16F10 cells contain putative neoepitopes matched to those carried by the Tarmogen vaccines. Tumor growth was monitored with digital calipers every other day through day 12. cI IN, intact yeast expressing a fusion of class I neoepitopes; cII IN, intact yeast expressing a fusion of class II neoepitopes; cI IN+cI YL, 1.25 YU of cI IN mixed with 1.25 YU of cI YL; cII IN+cII CL, 1.25 YU of cII IN mixed with 1.25 YU of cII YL. Days, number of days post-tumor challenge.

The result here shows that CL, when added to intact Tarmogen in an equivalent amount (1:1), increase the anti-tumor activity up to ~2 to 5 fold over intact Tarmogen alone.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to elicit a cytotoxic T cell immune response in a subject, the method comprising administering to the subject an immunogenic composition comprising:
   (i) a lysate prepared from a *Saccharomyces cerevisiae* yeast, wherein the lysate lacks yeast membranes and yeast cell walls;
   (ii) a whole *Saccharomyces cerevisiae* yeast; and
   (iii) at least one antigen that is heterologous to the yeast.

2. A method to elicit an antigen-specific humoral immune response and an antigen-specific cell-mediated immune response in a subject, said method comprising administering to the subject an immunogenic composition comprising:
   (i) a lysate prepared from a *Saccharomyces cerevisiae* yeast, wherein the lysate lacks yeast membranes and yeast cell walls;
   (ii) a whole *Saccharomyces cerevisiae* yeast; and
   (iii) at least one antigen that is heterologous to the yeast.

3. The method of claim 1, wherein the immunogenic composition further comprises an anti-CD40 antibody (Ab).

4. The method of claim 2, wherein the immunogenic composition further comprises an anti-CD40 Ab.

* * * * *

SEQUENCE LISTING

```
<160> NUMBER OF SEQ ID NOS: 10

<210> SEQ ID NO 1
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 1

Met Thr Glu Gln Gln Trp Asn Phe Ala Gly Ile Glu Ala Ala Ala Ser
1               5                   10                  15

Ala Ile Gln Gly
            20

<210> SEQ ID NO 2
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 2

Gln Pro Tyr Ser Gly Ser Pro Ala Asn Val Ala Val Tyr Thr Ala Leu
1               5                   10                  15

Val Glu Pro

<210> SEQ ID NO 3
```

```
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 3

Ser Gly Lys His Lys Tyr Arg Gln Thr Ala Met Phe Thr Ala Thr Met
1               5                   10                  15

Pro Pro Ala

<210> SEQ ID NO 4
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 4

Asn Arg Thr Ser Val Met Phe Asn Phe Pro Glu Gln Ala Thr Val Lys
1               5                   10                  15

Lys Val Val

<210> SEQ ID NO 5
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 5

Ser Phe Glu Thr Ala Ser His Asp Gly Glu Ala Gly Pro Ser Pro Glu
1               5                   10                  15

Val Leu Gln

<210> SEQ ID NO 6
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 6

Met Phe Asn Gln Gly Arg Ala Phe Ala Ala Val Arg Leu Pro Phe Cys
1               5                   10                  15

Gly His Lys

<210> SEQ ID NO 7
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 7

Leu Trp Val His Ser Leu Arg Arg Leu Leu Glu Cys Phe Tyr Val Ser
1               5                   10                  15

Val Phe Ser

<210> SEQ ID NO 8
<211> LENGTH: 19
<212> TYPE: PRT
<213> ORGANISM: Artificial Sequence
<220> FEATURE:
```

```
<223> OTHER INFORMATION: Synthetic Peptide

<400> SEQUENCE: 8

Glu Pro Met Phe Thr Phe Val Tyr Pro Thr Ile Phe Pro Leu Arg Glu
1               5                   10                  15

Thr Pro Met

<210> SEQ ID NO 9
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 9

Ser Ile Ile Asn Phe Glu Lys Leu
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 10

Met Ala Asp Glu Ala Pro
1               5
```